United States Patent [19]

Andrews et al.

[11] Patent Number: 5,015,641

[45] Date of Patent: May 14, 1991

[54] ANTIGLAUCOMA AGENTS

[76] Inventors: David R. Andrews, 111 Roland Ave., South Orange, N.J. 07079; Federico C. A. Gaeta, 5 Shawnee Ave., Rockaway Township, Morris County, N.J. 07866; Robert W. Watkins, Box 510B, R.R. #1, Great Meadows, N.J. 07838

[21] Appl. No.: 349,369

[22] Filed: May 9, 1989

Related U.S. Application Data

[60] Division of Ser. No. 892,003, Jul. 30, 1986, Pat. No. 4,885,293, which is a continuation-in-part of Ser. No. 784,000, Oct. 4, 1985, Pat. No. 4,826,816, and a continuation-in-part of Ser. No. 721,015, Apr. 8, 1985, Pat. No. 4,634,698, each is a continuation-in-part of Ser. No. 653,186, Apr. 24, 1984, Pat. No. 4,556,655.

[51] Int. Cl.$^5$ .............................................. A61K 31/54
[52] U.S. Cl. ............................... 514/223.5; 514/223.2
[58] Field of Search .................... 514/223.2, 223.5, 13, 514/19; 530/337, 800, 913

[56] References Cited

U.S. PATENT DOCUMENTS 4,634,698  1/1987  Andrews et al. .................. 514/913

OTHER PUBLICATIONS

The Merck Index, Tenth Ed., p. 1353 (1983).

*Primary Examiner*—Stanley J. Friedman
*Assistant Examiner*—Zohreh A. Fay
*Attorney, Agent, or Firm*—Joseph T. Majka; Anita W. Magatti; James R. Nelson

[57] ABSTRACT

Pharmaceutical compositions and a method for reducing intraocular pressure by topically applying a carboxyalkyl dipeptide are disclosed.

9 Claims, No Drawings

ANTIGLAUCOMA AGENTS

This is a division of application Ser. No. 892,003, filed July 30, 1986, which will issue as U.S. Pat. No. 4,885,293 and which is a continuation-in-part of Ser. No. 784,000 filed Oct. 4, 1985, now U.S. Pat. No. 4,826,816 and Ser. No. 721,015, filed Apr. 8, 1985, now U.S. Pat. No. 4,634,698, each of which are a continuation-in-part of Ser. No. 653,186, filed Sept. 24, 1984, now U.S. Pat. No. 4,556,655.

The present invention relates to ophthalmological methods and pharmaceutical compositions employing carboxyalkyl dipeptides joined through a sulfonamido group to a benzothiadiazinyl or sulfonylphenyl moiety.

BACKGROUND OF THE INVENTION

Glaucoma is an ocular disease complex associated with an elevated pressure within the eye (i.e., intraocular pressure, IOP). As a result of the elevated IOP, damage to the optic nerve head resulting in irreversible loss of visual function may ensue. Untreated, this condition may eventually lead to blindness.

Ocular hypertension, i.e., the condition of elevated intraocular pressure without optic nerve head damage or characteristic glaucomatous visual field loss, is now believed by the majority of ophthalmologists to represent the earliest phase in the onset of glaucoma.

A number of the drugs presently employed to treat glaucoma are not entirely satisfactory, particularly in the earliest course of the disease when the side effects they produce are often worse than the symptoms of the disease.

Epinephrine, used as a topical solution, must be utilized cautiously in patients with high blood pressure, diabetes, hyperthyroidism and cerebral artereosclerosis due to the possibility of systemic action.

Timolol, a clinically utilized, topically applied agent for lowering intraocular pressure, must be used with caution in patients in whom beta-adrenergic blockade may be undesirable. Systemic absorption of topically administered timolol and systemic beta-blockade are responsible for the contraindication of timolol therapy for glaucoma in patients with compromised pulmonary function and in patients who cannot tolerate its systemic cardiovascular action.

Pilocarpine, a topical drug, although considered systemically harmless and quite effective, may cause considerable local difficulties. Pupil constriction causes the eye to lose its ability to adapt from light to dark. Accommodation may become stimulated so that the patient's refraction is sometimes incorrect and vision becomes blurred. The drug itself may cause a local vasodilation and red eyes. Irritation is common.

Carbonic anhydrase inhibitors have been used systemically but they have a number of disadvantages. While effective in lowering intraocular pressure, they often cause a numbness and tingling, gastrointestinal upsets and, frequently, depression, lethargy, a loss of appetite, and central malaise. European Patent Application 81400326.5, Publication number 36,351 attempts to overcome these difficulties by the topical administration of an alkali metal salt of a carbonic anhydrase inhibitor.

The present invention provides a new composition and method for reducing and controlling elevated intraocular pressure, especially the elevated IOP associated with glaucoma.

SUMMARY OF THE INVENTION

The invention in a pharmaceutical composition aspect involves a topical ophthalmologically acceptable composition useful for reducing and controllinq elevated intraocular pressure, especially elevated IOP associated with glaucoma, which comprises an intraocular pressure reducing effective amount of a compound of formula I as described below in combination with an ophthalmologically acceptable carrier for topical use. The invention in a pharmaceutical method aspect involves a method for controlling elevated intraocular pressure in an eye, especially elevated IOP associated with glaucoma in a human eye, which method comprises administering to said eye an intraocular pressure reducing effective amount of a compound of formula I. Such method and composition may also be used in conjunction with the administration of a beta-adrenergic blocking agent and/or an anti-inflammatory steroid.

The compounds contemplated for use in the compositions and methods of this invention have the following structural formula I:

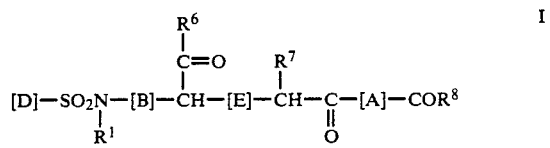

or a pharmaceutically acceptable salt thereof, wherein:
A is

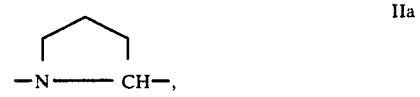

IIa

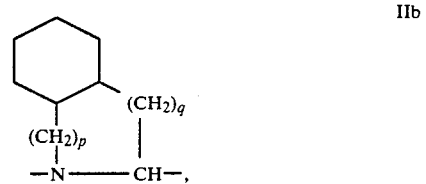

IIb

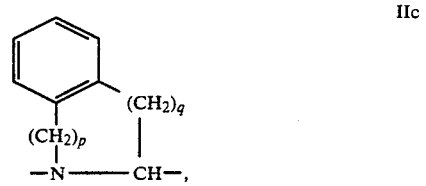

IIc

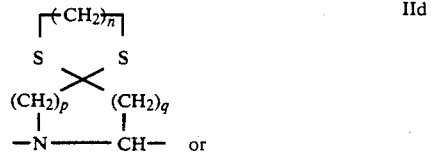

IId

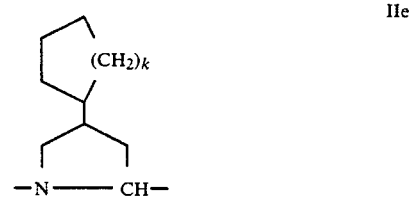

IIe k is 1 or 2;
n is 0 or 1;
p and q are 0, 1 or 2, provided that in structures IIb and IIc the sum of p and q is 1 or 2, and that in formula IId, p is not 0;
B is —[J]—[L]—[M]—;
D is IIIa        IIIb E is —NH—, —O—, —S—, or —CH$_2$—;
G is $$-\underset{\underset{O}{\|}}{C}- \text{ or}$$

—SO$_2$—;
J is —(CH$_2$)$_s$— or —((CH$_2$)$_t$—W)—;
L is a chemical bond, cis- or trans-lower alkenylene, lower alkynylene, -Z-aryl-, -aryl-Z-, -Z-cycloalkyl-, or -cycloalkyl-Z-, a 5- or 6-membered heterocyclic radical comprising 3 to 5 carbon atoms and 1 or 2 heteroatoms selected from N, O and S, or a R$^5$-substituted heterocyclic radical, wherein aryl is and cycloalkyl is wherein
w is 1, 2 or 3:
M is —(CH$_2$)$_u$— or —((CH$_2$)$_t$—X—(CH$_2$)$_v$)—;
W is $$-\overset{O}{\underset{\|}{C}}NH- \text{ or } -NH\overset{O}{\underset{\|}{C}}-;$$

X and Z are independently a chemical bond, —NR$^9$—, —O—, —S—, $$-\overset{O}{\underset{\|}{C}}NH- \text{ or } -NH\overset{O}{\underset{\|}{C}}-;$$

s, u and v are independently 0-5;

t is 1-5;
R$^1$, R$^2$ and R$^9$ are independently hydrogen, lower alkyl or lower acyl;
R$^3$ is hydrogen, lower alkyl, halo- and dihaloloweralkyl, trifluoroethylthiomethyl, phenylloweralkyl, (cycloalkyl)lower-alkyl, aminomethyl, lower alkylaminomethyl, phenylloweralkylaminomethyl,-(cycloalkyl)loweralkylaminomethyl, loweralkylthiomethyl, haloloweralkylthiomethyl, 2-,3- or 4-pyridylloweralkyl, 2-, 4- or 5-thiazolylloweralkyl, 2-, 4- or 5-1H-imidazolylloweralkyl, 1-imidazolylloweralkyl, 1-morpholinoloweralkyl or hydroxyphenylloweralkyl;
R$^4$ is chlorine or CF$_3$;
R$^5$ is hydrogen, halogen, lower alkyl, lower acyl, lower alkoxy, haloloweralkyl or phenylloweralkyl;
R$^7$ is hydrogen, lower alkyl or aminoloweralkyl;
R$^6$ and R$^8$ are independently hydroxy, alkoxy having from 1 to 8 carbon atoms, benzyl, allyl, R$^{10}$—Q—$_r$—(CH$_2$)$_m$—O—, wherein Q is oxygen or sulfur, r is 0 or 1 and m is 2 to 4, $$-O\overset{R^{11}}{\underset{|}{C}}H-OCO\text{-alkyl}$$

wherein the alkyl has from 3 to 8 carbon atoms, $$-O\overset{R^{11}}{\underset{|}{C}}HCO\text{-phenyl}$$

wherein the phenyl may be substituted with group T defined, below, 1-glyceryl,

R$^{10}$ is phenyl, substituted phenyl wherein the substituents are chosen from group T, 1-naphthyl or 2-naphthyl;
T is halogen, hydroxy, trifluoromethyl, lower alkoxy, lower alkyl, 2-furanyl, 3-furanyl, 2-thienyl, 3-thienyl, phenyl and substituted phenyl wherein the substituents are chosen from halogen, hydroxy, trifluoromethyl, lower alkoxy or lower alkyl;
R$^{11}$ is hydrogen or alkyl having from 1 to 8 carbon atoms;
R$^{12}$ is hydrogen, lower alkyl, unsubstituted or substituted phenyl and substituted or unsubstituted phenyl lower alkyl wherein phenyl may be substituted by group T; and
R$^{13}$ is hydrogen or lower alkyl;
provided that if L is alkenylene or alkynylene, J is —(CH$_2$)$_s$— wherein s is 1-5; provided that if L is -Z-aryl- or -Z-cycloalkyl-, J is —(CH$_2$)$_s$— wherein s is 2-5; provided that if L is alkenylene, alkynylene, -aryl-Z- or -cycloalkyl-Z-, M is —(CH$_2$)$_u$— wherein u is 1-5; provided that if s and u are each zero, L is aryl or cycloalkyl (i.e. Z is a bond); and provided that if s and v are each zero, L is aryl or cycloalkyl (i.e. Z is a bond); and
with the further provisos that, when D is of formula IIIb and R$^1$ is hydrogen, B is not —(CH$_2$)$_4$—; and that, when D is of formula IIIb and $R^1$ is hydrogen or lower alkyl, B is not —$(CH_2)_s$—aryl—$(CH_2)_t$—X—$(CH_2)_v$— wherein s is 0 or 1, t is 1, v is 0 to 2 and X is a bond, —O—, or —S—.

The invention in another aspect involves two kits for use in reducing and controlling elevated intraocular pressure. Both kits comprise first and second containers, in a single package, wherein in both cases the first container includes a topical pharmaceutical composition comprising an IOP reducing effective amount of a compound of formula I. In a first kit, the second container includes a pharmaceutical composition comprising an anti-inflammatory effective amount of a steroid in a pharmaceutically acceptable carrier. In the second kit, the second container includes a pharmaceutical composition comprising an intraocular pressure reducing amount of a beta adrenergic blocking agent in a topical opthamological carrier.

DETAILED DESCRIPTION

The compounds employed in the method and composition of the present invention are the subject matter of Ser. No. 721,015, filed Apr. 8, 1985; Ser. No. 784,000, filed Oct. 4, 1985; and Ser. No. 653,186, filed Sept. 24, 1984, which issued as U.S. Pat. No. 4,556,655, the disclosures of which are incorporated herein by reference.

When A is formula IIb or IIc, the preferred sum of p and q is 1; when A is of formula IId, preferred values for each of p and q are 1. Compounds wherein A is IIa or IIb wherein p is 0 and o is 1, and IId wherein p and q are each 1 and n is zero are preferred.

Also preferred are compounds wherein D is of formula IIIa, with compounds wherein $R^4$ is chlorine and G is —$SO_2$— being more preferred. Another group of preferred compounds are those wherein D is of formula IIIa, $R^4$ is chlorine, G is —$SO_2$—, $R^2$ is preferably hydrogen and $R^3$ is preferably phenylethyl, (cyclopentyl)methyl, chloromethyl, dichloromethyl, 2-pyridinylethyl, butyl, pentyl, or trifluoroethylthiomethyl.

Also preferred are compounds wherein B is

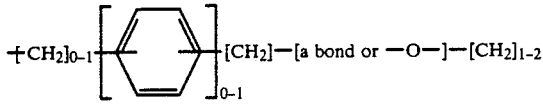

i.e., compounds wherein J is —$(CH_2)_s$— and s is 0–1, L is a bond or -Z-aryl- wherein Z is a bond, and M is —$((CH_2)_t$—X—$(CH_2)_v)$, wherein t is 1, v is 1–2, and X is a bond or —O—.

For compounds wherein L is a heterocyclic radical, thiazolyl rings joined to the rest of molecule at the 2,4 and 2,5 positions are preferred.

A preferred group for E is —NH—.

Another group of preferred compounds are those wherein $R^7$ is hydrogen, methyl or aminobutyl. Still another group of preferred compounds are those wherein $R^6$ and $R^8$ are hydroxy, ethoxy, methoxy, phenoxyethoxy, 1-glyceryl, pivaloyloxyalkyloxy, and

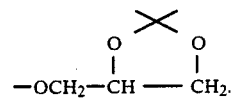

A preferred group of compounds are those represented by the general formula

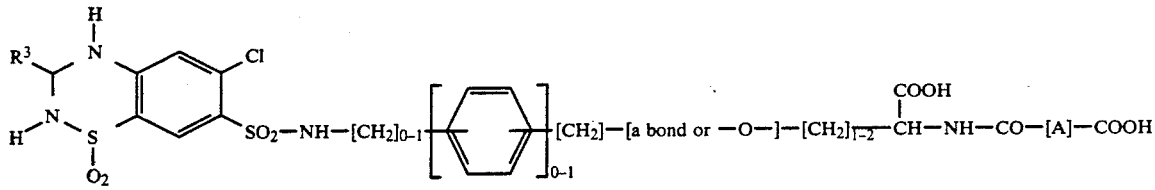

wherein $R^3$ is phenylethyl, chloromethyl, dichloromethyl, butyl, pentyl, (cyclopentyl)methyl, trifluoroethylthiomethyl or 2-pyridinylethyl.

As used herein, "lower alkyl" means straight or branched chain hydrocarbon radicals of from 1 to 6 carbons, e.g. methyl, ethyl, propyl, isopropyl, butyl, t-butyl, pentyl and hexyl. Similarly, "lower alkoxy" means straight or branched alkoxy radicals having from 1 to 6 carbon atoms, e.g. methoxy, ethoxy, propoxy, butoxy, iso-butoxy, pentoxy and hexyloxy. "Halogen" means fluorine, chlorine and bromine. "Lower acyl" means organic radicals obtained by removing the hydroxyl group from the corresponding carboxylic acid of from 1 to 6 carbons, e.g. formyl, acetyl, propionyl and butyryl. "Lower alkenylene" means unsaturated hydrocarbon radicals of from 2 to 6 carbon atoms having one double bond, e.g. vinylene, propenylene, butenylene, pentenylene and hexenylene wherein the double bond may be present anywhere in the chain, e.g. 1- or 2- propenylene, 1-, 2- or 3-butenylene. Similarly, "lower alkynylene" means a hydrocarbon radical of from 2 to 6 carbon atoms having one triple bond, e.g. ethynylene, propynylene, butynylene, pentynylene and hexynylene, wherein the triple bond may be present anywhere in the chain, e.g. 1- or 2- propynylene, 1-, 2- or 3-butynylene.

Example of heterocyclic radicals are:

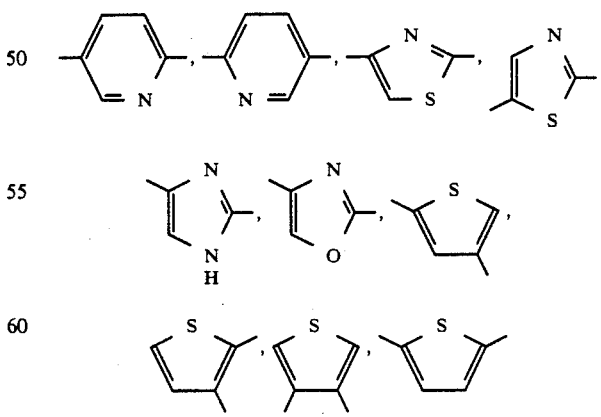

Compounds of the instant invention include various stereoisomers. Preferred stereoisomers are those in which the absolute configuration at carbon atoms adjacent to both a nitrogen and a carbonyl group corresponds most closely to the absolute configuration of L-amino acids.

Preferred examples of compounds of formula I are as follows:

1-[2-(S)-[[1-(S)-carboxy-2-[4-[[[6-chloro-3-(chloromethyl)-3,4-dihydro-2H-1,2,4-benzothiadiazin-7-yl]sulfonylamino]methyl]phenylmethoxy]ethyl]amino]-1-oxopropyl]-[2S-(2α, 3aα, 7aα)]-octahydro-1H-indole-2-carboxylic acid, S,S-dioxide, 1-[2-(S)-[[1-(S)-carboxy-2-[4-[[[6-chloro-3-(chloromethyl)-3,4-dihydro-2H-1,2,4-benzothiadiazin-7-yl]sulfonylamino]methyl]phenylmethoxy]ethyl]-(S)-alanyl-(S)-proline,S,S-dioxide, 1-[2-(S)-[[1-(S)-carboxy-3-[4-[[[6-chloro-3-(chloromethyl)-3,4-dihydro-2H-1,2,4-benzothiadiazin-7-yl]sulfonylamino]methyl]phenyl]propyl]amino]-1-oxopropyl]-[2S-(2S-(2α, 3aα, 7aα)]-octahydro-1H-indole-2-carboxylic acid, S,S-dioxide, N-[1-(S)-carboxy-3-[4-[[[6-chloro-3-(chloromethyl)-3,4-dihydro-2H-1,2,4-benzothiadiazin-7-yl]sulfonylamino]methyl]phenyl]propyl]-(S)-alanyl-(S)proline, S,S-dioxide, N-[1-(S)-carboxy-4-[4-[[[6-chloro-3-(chloromethyl)-3,4-dihydro-2H-1,2,4-benzothiadiazin-7yl]sulfonylamino]methyl]phenyl]butyl]-(S)-alanyl-(S)proline, S,S-dioxide, 7-N-[2-(S)-[[1-(S)-carboxy-3-[4-[[[6-chloro-3-(chloromethyl)-3,4-dihydro-2H-1,2,4-benzothiadiazin-7-yl]sulfonylamino]methyl]phenyl]propyl]amino]-1oxopropyl]-1,4-dithia-7-azaspiro,[4.4]nonane-8-(S)-carboxylic acid, S,S-dioxide, N-[1-(S)-carboxy-5-[6-chloro-3-(chloromethyl)-3,4-dihydro-2H-1,2,4-benzothiadiazin-7-yl]sulfonylamino]pentyl-(S)-alanyl-(S)-proline, S,S-dioxide, 1-[2-(S)-[[1-(S)-carboxy-5-[[-6-chloro-3-(chloromethyl)-3,4-dihydro-2H-1,2,4-benzothiadiazin-7-yl]sulfonylamino]pentyl]amino]-1-oxopropyl]-[2S-(2α, 3aα, 7aα)]-octahydro-1H-indole-2-carboxylic acid, S,S-dioxide, and the 3-(dichloromethyl)-,3-(cyclopentylmethyl)-,3-(2-phenylethyl)-, 3-(butyl)-,3-(pentyl)-, and 3-(trifluoroethylthiomethyl)-1,2,4-benzothiazinyl analogues thereof.

The compounds of this invention form salts with various inorganic and organic acids and bases which are also within the scope of the invention. Such salts include ammonium salts, alkali metal salts, e.g. sodium and potassium salts, and alkaline earth metal salts, e.g. calcium and magnesium salts. Salts with organic bases may be prepared, e.g., N-methylglucamine, lysine and arginine, as well as salts with organic and inorganic acids, e.g., HCl, HBr, H$_2$SO$_4$, H$_3$PO$_4$, methanesulfonic acid, toluenesulfonic acid, maleic acid, fumaric acid and camphorsulfonic acid. The non-toxic pharmaceutically acceptable salts are preferred, although other salts are also useful, e.g., in isolating or purifying the product. The acid salts (e.g. HCl and maleate) are preferred, especially the hydrochloride.

The salts may be formed by conventional means, as by reacting the free acid or base forms of the product with one or more equivalents of the appropriate base or acid in a solvent or medium in which the salt is insoluble, or in a solvent such as water which is then removed in vacuo, or by exchanging the cations of an existing salt for another cation on a suitable ion exchange resin.

Compounds of formula I may be prepared by several routes using methods known in the art.

For example, compounds of formula I can be prepared by condensing an acid of formula IV (or its hydrochloride salt) with an amino acid derivative of formula V:

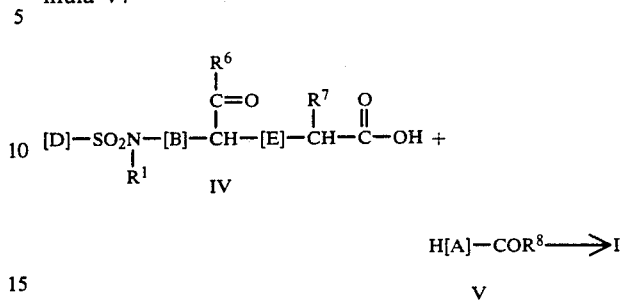

wherein $R^1$, $R^6$, $R^7$, $R^8$, D, B, E and A are as defined above. The reaction is carried out in an inert solvent such as dimethylformamide (DMF) in the presence a condensing agent such as 1-(3-dimethylaminopropyl)-3-ethyl carbodiimide hydrochloride (DEC) and 1-hydroxybenzotriazole, and where the compound of formula IV is a salt in the presence of a base such as triethylamine. The reaction is preferably carried out in an inert atmosphere at a temperature of 0°-25° C.

Compounds of formula V are known in the art, or may be prepared by methods well known to those skilled in the art.

Compounds of formula IV may be prepared for example from the reaction of a sulfonyl chloride of formula VI and an amine of formula VII:

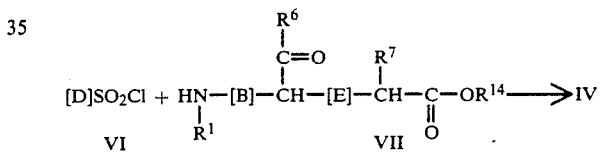

wherein D, B, E, $R^1$, $R^6$ and $R^7$ are as defined above and $R^{14}$ is a readily removable ester protecting group such as t-butyl, benzyl or trimethylsilylethyl. The reaction is carried out at 0°-5° C. in a solvent such as tetrahydrofuran (THF).

Compounds of formula VI may be prepared from know starting materials using procedures well known in the art. For example, when D is of the formula IIIa wherein G is SO$_2$ and $R^3$ is phenylethyl, the sulfonyl chlorides of formula VI may be obtained by reacting a disulfonyl chloride of formula VIII with aqueous ammonia at low temperature (dry-ice-acetone bath) in a solvent such as 1,2-dimethyoxyetane (DME) in the presence of a base such as triethylamine to obtain a sulfamide of formula IX, followed by reaction of the sulfoamide with phenyl propanal in a solvent such as DME and in the presence of an acid such as p-tolenesulfonic acid:

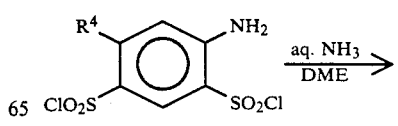

VIII

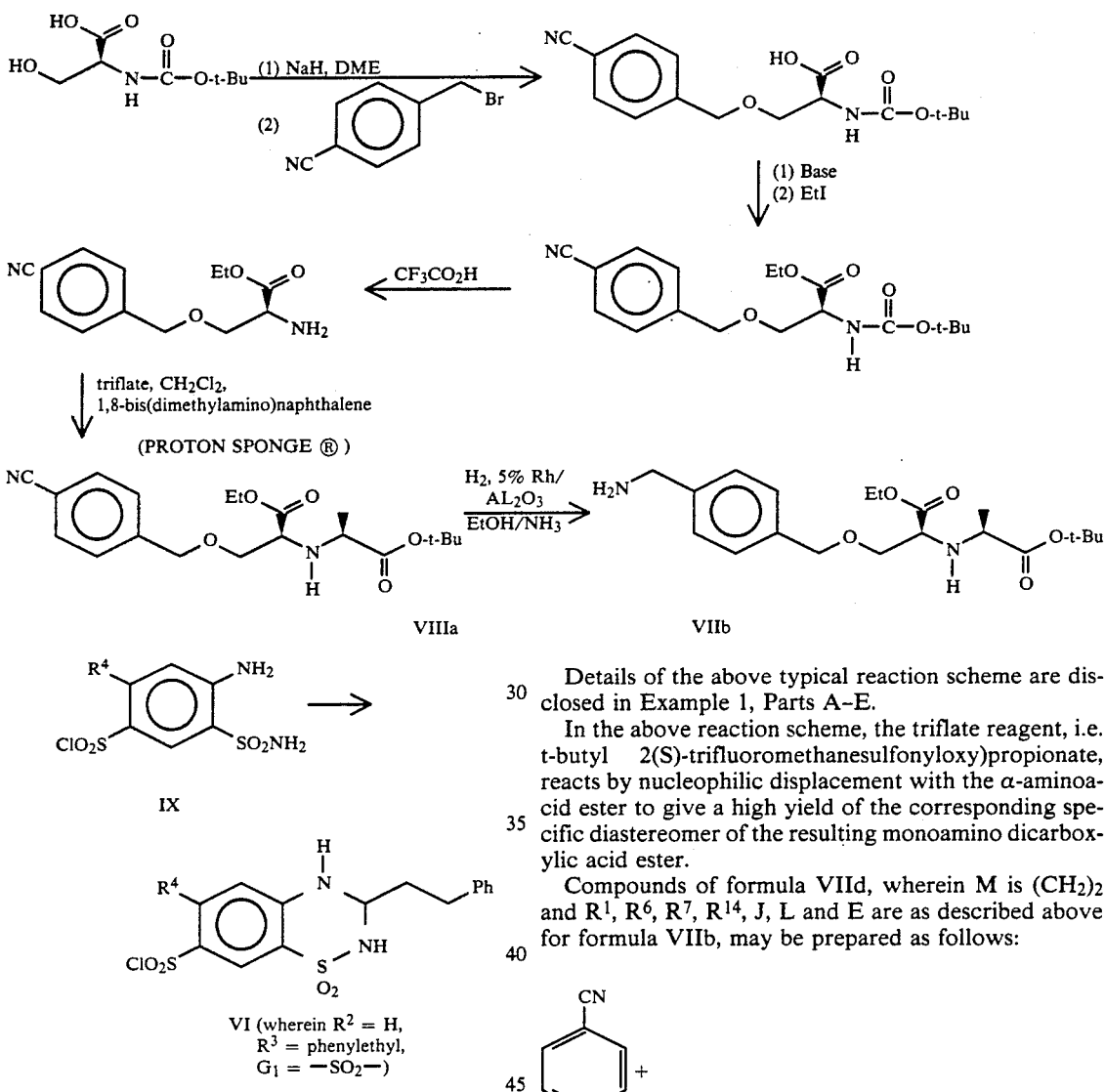

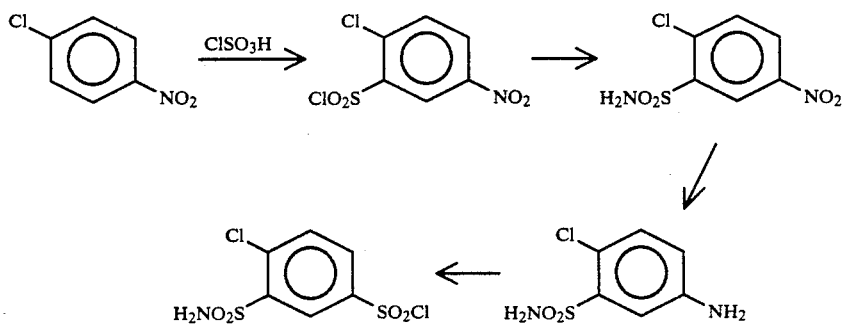

Similarly, when D is of formula IIIb, the sulfonyl chlorides of formula VI may be obtained by well known procedures. A typical reaction scheme was follows:

Compounds of formula VII are prepared from known started materials using methods known in the art. A typical reaction scheme is shown below for compounds of formula VIIb, wherein $R^1$ is hydrogen, $R^6$ is lower alkyl, $R^7$ is methyl, J is —(CH$_2$)—, L is phenyl, M is —CH$_2$—O—CH$_2$—, E is —NH—, and $R^{14}$ is as defined above:

Details of the above typical reaction scheme are disclosed in Example 1, Parts A–E.

In the above reaction scheme, the triflate reagent, i.e. t-butyl 2(S)-trifluoromethanesulfonyloxy)propionate, reacts by nucleophilic displacement with the α-aminoacid ester to give a high yield of the corresponding specific diastereomer of the resulting monoamino dicarboxylic acid ester.

Compounds of formula VIId, wherein M is (CH$_2$)$_2$ and $R^1$, $R^6$, $R^7$, $R^{14}$, J, L and E are as described above for formula VIIb, may be prepared as follows:

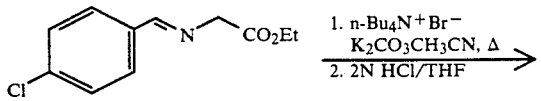

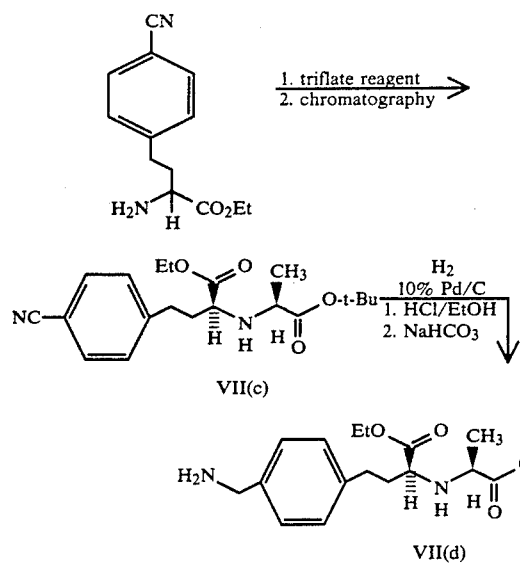

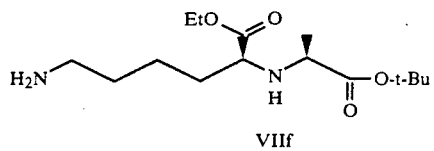

The above reaction scheme is exemplified in Parts A-C of Example 3.

A typical reaction scheme for the preparation of compounds of formula VIIf wherein L is a bond, J is —(CH$_2$)$_s$— and M is —(CH$_2$)$_u$— wherein the sum of s and u is 4, and R$^1$, R$^6$, R$^7$, R$^{14}$ and E are as described above for formula VIIb is as follows:

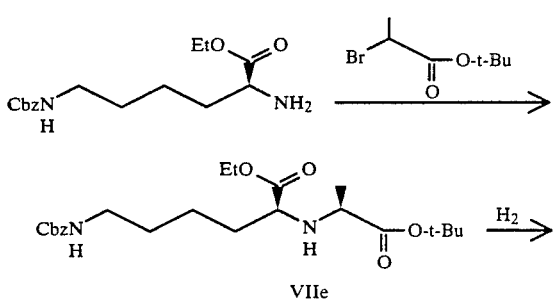

Example 5 provides details of this procedure.

Alternatively, intermediates of formulae VIIa or VIIc may be used to prepare compounds of formula I as follows: The R$^{14}$ protecting groups (e.g. t-butoxycarbonyl) of compounds of formulae VIIa or VIIc may be removed, e.g. by trifluoroacetic acid, and the nitrile reacted with an amino acid derivative of formula V under the conditions described on page 12. The resulting nitrile can then be reduced to the corresponding amine, e.g., by hydrogenation, which amine can then in turn be coupled to a sulfonyl chloride of formula VI by conventional methods. Similarly, intermediates of formula VIIe (i.e., compounds of formula VII wherein B is alkyl) may be deprotected at the carboxylic acid group and condensed with the amino acid derivative of formula V as described above, then deprotected at the amino group, e.g. by hydrogenation, and the resultant amine reacted with a sulfonyl chloride of formula VI by conventional methods.

Another method for preparing compounds of formula IV is that exemplified below for preparing compounds wherein D is of formula IIIa wherein G is —SO$_2$—, J is —CH$_2$—, is -aryl-Z- wherein aryl is phenyl and Z is

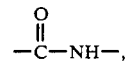

M is —CH$_2$—, E is —NH—, R$^1$ is hydrogen, R$^6$ is ethyl, R$^7$ is methyl, and R$^2$, R$^3$ and R$^4$ are as defined above:

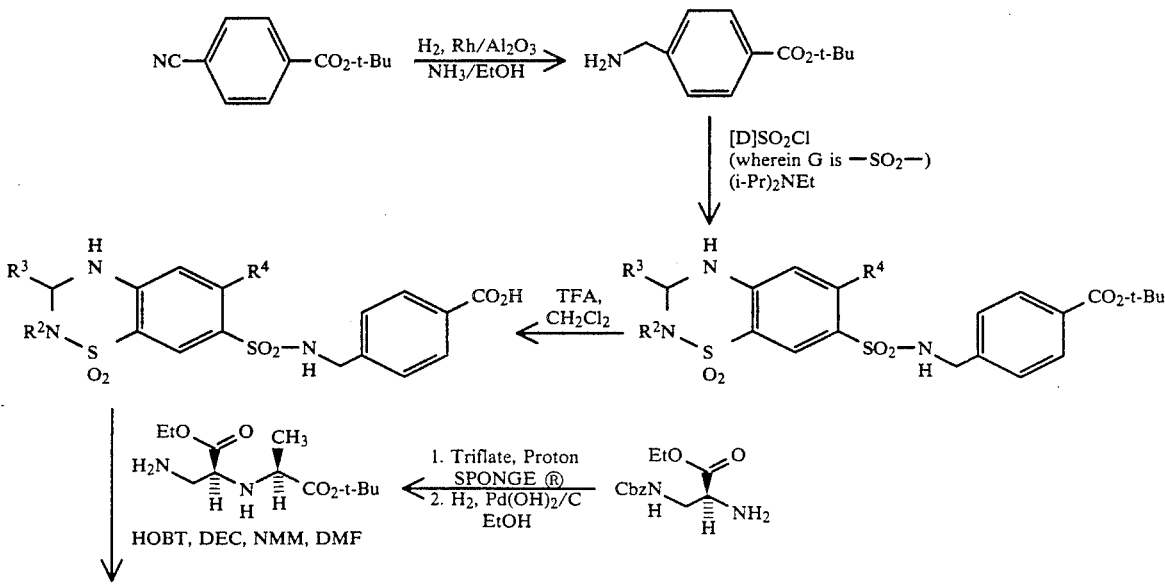

-continued

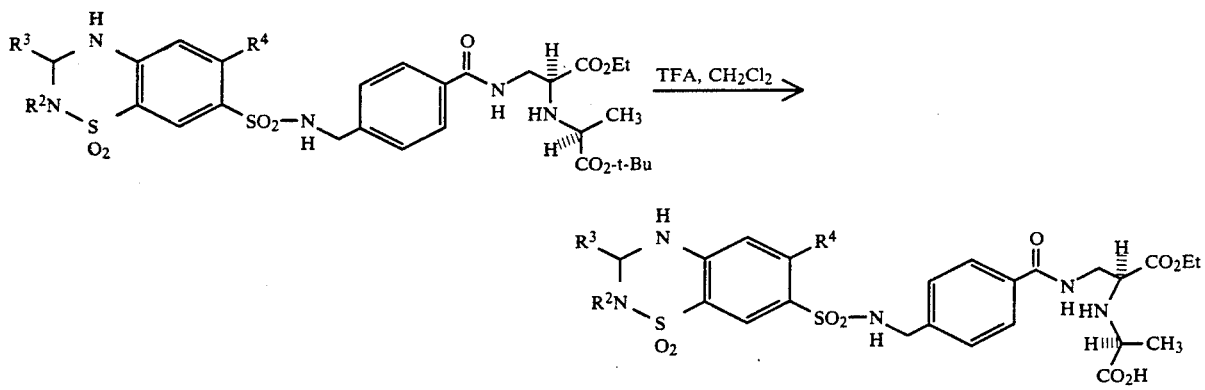

Another method for the preparation of compounds of formula I involves the sulfonylation of an amine of formula X with a sulfonylchloride of formula VI:

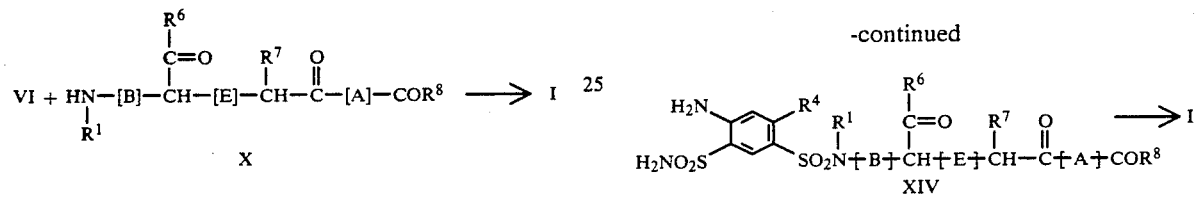

wherein $R^1$, $R^6$, $R^7$, $R^8$, B, E and A are as defined above. The reaction is carried out in an inert solvent such as THG in the presence of a proton acceptor such as N-methylmorpholine. The reaction is preferably carried out in an inert atmosphere at a temperature of 0°–25° C.

Compounds of formula X may be prepared by well known methods, for example to obtain compounds wherein B is —$CH_2$—$C_6H_5$—$(CH_2)_2$—, E is —NH— and $R^1$, $R^6$, $R^7$ and $R^8$ are as defined above, compounds of formula VII(c) may be deprotected at the terminal carboxy group and then condensed with an amino acid of formula V:

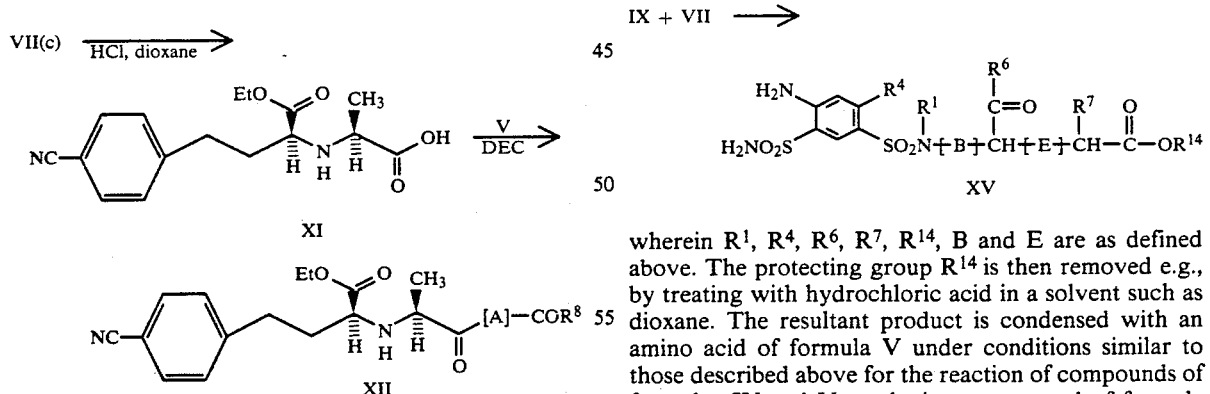

The nitrile of formula XII is reduced to an amine of formula X, e.g. by hydrogenation.

Compounds of formula I may also be prepared by condensing an aldehyde of formula XIII (or a reaction derivative thereof, e.g., an acetal) with an aminosulfonamide of formula XIV:

$R^3$—CHO +
XIII

-continued

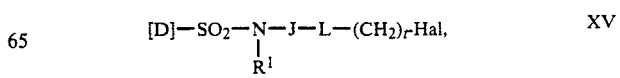

wherein $R^1$, $R^3$, $R^4$, $R^6$, $R^7$, $R^8$, B, E and A are as defined above. The reaction is carried out in an inert solvent such as THF in the presence of p-toluenesulfonic acid. The reaction is preferably carried out in an inert atmosphere at a temperature of 0°–80° C.

Compounds of formula XIII are known in the art or may be prepared by known methods.

Compounds of formula XIV can also be prepared by known methods, for example a sulfonamide of formula IX can be reacted with an amine of formula VII to obtain a compound of formula XV:

IX + VII ⟶

$$H_2N\underset{H_2NO_2S}{\diagdown}\!\!\!\overset{R^4}{\diagdown}\!\!\!-SO_2N\!\!\underset{R^1}{-}\!\!\{B\}\!\!-\!\!CH\!\!\{E\}\!\!-\!\!\overset{R^7}{CH}\!\!-\!\!\overset{O}{\underset{\|}{C}}\!\!-\!\!OR^{14}$$
XV wherein $R^1$, $R^4$, $R^6$, $R^7$, $R^{14}$, B and E are as defined above. The protecting group $R^{14}$ is then removed e.g., by treating with hydrochloric acid in a solvent such as dioxane. The resultant product is condensed with an amino acid of formula V under conditions similar to those described above for the reaction of compounds of formulae IV and V to obtain a compound of formula XIV.

Yet another process for the preparation of the compounds of the formula I wherein X is sulfur comprises condensing a halide of the general formula XV $$[D]-SO_2-N-J-L-(CH_2)_r-Hal, \qquad XV$$
$$\phantom{[D]-SO_2-N}|\phantom{-J-L-(CH_2)_r-Hal,}$$
$$\phantom{[D]-SO_2-N-}R^1$$

with a thiol of the general formula XVI

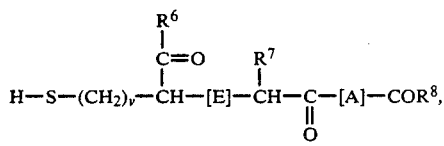 XVI where $R^1$, $R^6$, $R^7$, $R^8$, A, E, J, L, t and v are as defined for formula I and Hal represents halogen, preferably bromine. The reaction is preferably carried out in an inert medium at a temperature of 0°–25° C.

Compounds of the formula XV may be prepared by well known methods. Illustrative of such methods, is the following specific reaction scheme:

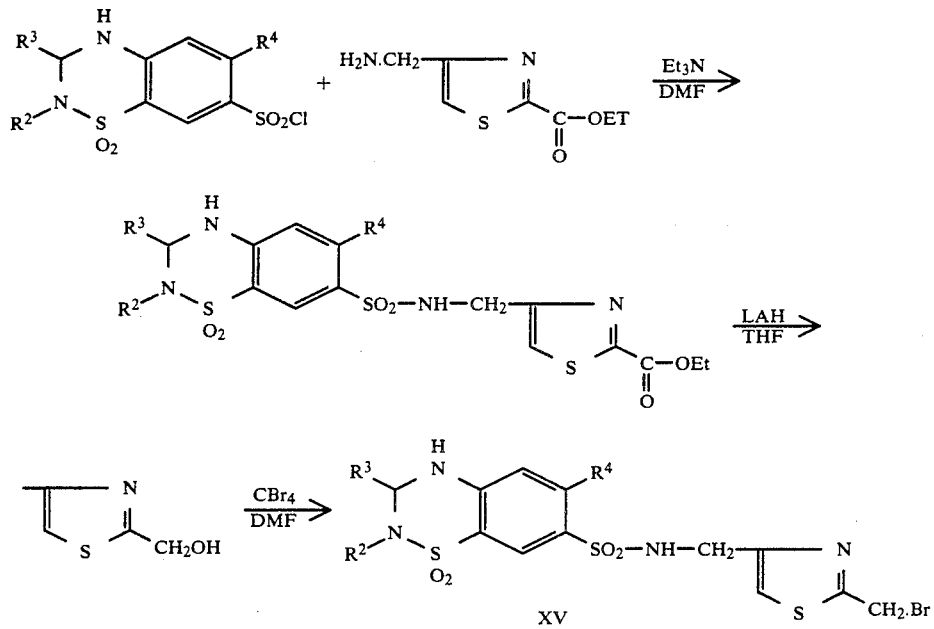

(wherein D is IIIa wherein G is SO$_2$, J is —(CH$_2$)$_5$— wherein 5 is 1, L is 2-thiazolyl, t is 1, $R^1$ is hydrogen, and Hal is bromine)

Compounds of general formula XVI may also be prepared by known methods, the following specific reaction scheme being illustrative of such methods:

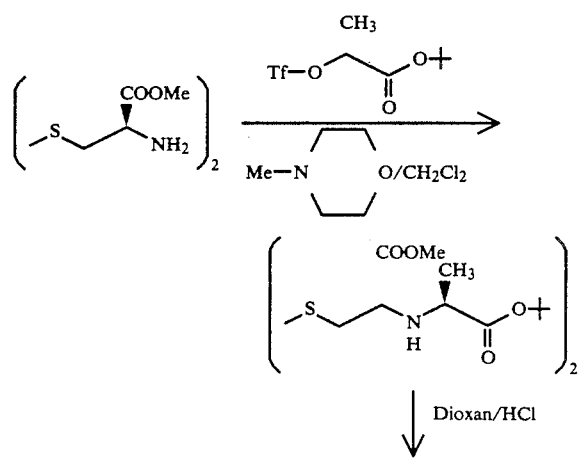

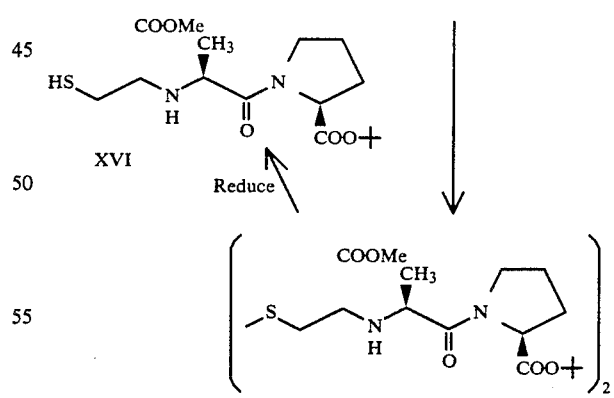

(wherein v is 1, E is —NH—, A is IIa, $R^6$ and $R^7$ are each —CH$_3$, and $R^8$ is t-butyl)

The known coupling methods above include amino group protection during the coupling reaction, for example with protecting groups such as N-formyl, N-t-butoxycarbonyl (t-Boc) and N-carbobenzyloxy (Cbz) groups, followed by their removal to yield compounds of formula I. Furthermore, the COR$^8$ function wherein $R^8$ is OH may be protected by removable ester groups such as benzyl, ethyl, t-butyl, trimethylsilylethyl and the like.

The more complex esters at $R^6$ (i.e., $R^6$ is other than hydroxy or alkoxy) are most conveniently prepared by esterifying compounds of formula I wherein $R^6$ is hydroxy and $R^8$ is a protected hydroxy, e.g. benzyloxy, with the appropriate reagents, e.g. chloromethyl pivalate in the presence of base, to obtain the corresponding pivaloyloxymethyl ester; the benzyl group is then removed by conventional means, e.g. catalytic hydrogenation.

hyroxyethyl cellulose, ethyl oleate, carboxymethyl cellulose, polyvinylpyrrolidone, and other water soluble ophthalmologically acceptable non-toxic polymers, for example, cellulose derivatives such as methyl cellulose, alkali metal carboxymethyl cellulose, hydroxyethyl cellulose, hydroxypropyl cellulose, hydroxypropylmethyl cellulose; acrylates such as polyacrylic acids salts, ethylacrylates; polyacrylamides; natural products such as gelatin, alginates, pectins, tragacanth, karaya, chondrus, agar, acacia; the starch derivatives such as starch acetate, hydroxyethyl starch ethers, hydroxpropyl starch, as well as other synthetic derivatives such as polyvinyl alcohol, polyvinyl pyrrolidone, polyvinyl meyhyl ether, polyethylene oxide, neutralized carbopol and xanthan gum and mixtures of these polymers. The pharmaceutical preparation may also contain non-toxic auxiliary substances such as emulsifying, preserving, wetting, bodying agents and the like, as for example, polyethylene glycols 200, 300, 400 and 600, carbowaxes 1,000, 1,500, 4,000, 6,0000 and 10,000, antibacterial components such as quaternary ammonium compounds; phenylmercuric salts known to have cold sterilizing properties and which are non-injurious in use; thimerosal, methyl and propyl paraben, benzyl alcohol, phenyl ethanol; buffering ingredients such as alkali metal chloride, borate, acetate, gluconate buffers; antioxidants such as sodium metabisulfite, butylated hydroxyanisole (BHA), butylated hydroxytoluene (BHT) and the like; and other conventional ingredients such as sorbitan monolaurate, triethanolamine, oleate, polyoxyethylene sorbitan monopalmitylate, dioctyl alkali metal sulfosuccinate, monothioglycerol, ethylenediamine tetracetic acid and the like.

When topically administered to the eye, the compounds employed in the invention reduce intraocular pressure (IOP). For example, 1-[2-(S)-[[1-(S)-carboxy-5-[[6-chloro-3-chloromethyl-3,4-dihydro-2H-1,2,4-benzothiadiazinyl-7-yl]sulfonylamino]-pentyl]amino]-1-oxopropyl]-[2S-(2α,3aα,7aα)]-octahydro-1H-indole-2-carboxylic acid, S,S-dioxide caused falls in IOP of a magnitude similar to those produced by the antiglaucoma agent timolol when each were administered at concentrations of 0.00001 and 0.5 (w/v %), respectively, and tested by the following procedure:

Male New Zealand white rabbits having a normal IOP are conditioned to the laboratory setting for at least one 4 hr period before being used to study drug effects. A Makay-Marg applanation tonometer is used to measure IOP. Readings, in mm Hg, are taken in triplicate and the average is recorded.

Rabbits are restrained in a cloth sack 2 min. prior to IOP determination. The left lower eyelid is retracted to form a pouch and 1 drop of a local anesthetic is irrigated over the cornea. The lower eyelid is then held closed over the eye for about 1 min. Corneal anesthesia is repeated before each set of IOP determinations. Readings are taken just before dosing with drug (0 time) and at hourly intervals thereafter. Drugs are administered in a 50 μl volume in the same manner as the anesthetic.

To prepare suitable dosage forms, the active compounds may be conveniently admixed with a non-toxic pharmaceutically acceptable carrier suitable for topical ophthalmologic administration. Typical of such pharmaceutically acceptable carriers are, for example, water, mixtures of water and water miscible solvents such as lower alkanols or vegetable oils, petroleum based jelly, and including also from 0.1 to 2% by weight of Additionally, suitable ophthalmic vehicles can be used as carrier media for the present purpose including conventional phosphate buffer vehicle systems, isotonic boric acid vehicles, isotonic alkali chloride vehicles, tris and the like.

The pharmaceutical preparation may also be in the form of a solid insert. For example, one may use a solid water soluble polymer as the carrier for the medicament. Inserts that are known in the art that are suitable for this use include those described in British Patent 15611, and in U.S. Pat. Nos. 3,993,071; 3,986,510; 3,868,445; and 3,867,510. Solid water insoluble inserts, such as those prepared from ethylene vinyl acetate copolymer, may also be utilized.

The compositions of the invention may include therapeutically effective amounts of additional ophthamologically acceptable therapeutic agents in addition to the compound of formula I. For example antibiotics and anesthetics, as well as other IOP lowering agents may be present.

The pharmaceutical compositions of the invention are administered in the form of ophthalmic pharmaceutical compositions adapted for topical administration to the eye; such as solutions, suspensions, ointments and solid inserts. Formulations of the invention may contain from about 0.000001% (w/v) to about 1.0% and especially about 0.00001% to about 0.01% of a compound of formula I. As a unit dosage form, between about 0.5 ng to about 0.05 mg preferably 5 ng to 5 μg of such compound is applied to the human eye.

Where utilized herein, the term "controlling the elevated intraocular pressure" means the regulation, attenuation and modulation of increased intraocular tension, which is the primary diagnostic symptom of the disease glaucoma. The term also means that the diminution, in the otherwise elevated intraocular pressure, obtained by the practice of the invention is maintained for a significant period of time as, for example, between consecutive doses of the composition of the invention.

The compounds of formula I may be employed in the composition and methods of the invention as the sole IOP lowering ingredient or may be used in combination (in the same or separate compositions) with other mechanistically distinct IOP lowering ingredients such as beta-adrenergic blocking agents, (e.g., timolol). For purposes of the present invention, the term beta-adrenergic blocker means a compound which by binding to beta adrenergic plasma membrane receptors reduces or eliminates sympathetic activity or blocks the effects of exogenously administered catecholamines or adrenergic drugs. See, for example, Weiner, N., Drugs That Inhibit Adrenergic Nerves and Block Adrenergic Receptors, in *The Pharmaceutical Basis of Therapeutics* (ed. A. G. Goodman, L. S. Goodman, A. Gilman), Macmillan Publishing, New York, 1980, 6th ed., pp. 188-197. Examples of preferred beta adrenergic blockers are bunolol (5-[3-(1,1-dimethylethyl)amino-2-hydroxypropoxy]-3,4-dihydro-1(2H)-naphthalenone), atenolol (4-[2-hydroxy-3-[(1methylethyl)amino]-propoxy]benzeneacetamide), metoprolol (1-[4-(2-methoxyethyl)-phenoxy]-3-[(1-methylethyl)amino]-2-propanol), nadolol (5-[3-[(1,1-dimethylethyl)amino]-2-hydroxypropoxy]-1,2,3,4-tetrahydro-2,3-naphthalenediol), pindolol (1-(1H-indol-4-yloxy)-3-[(1-methylethyl)amino]-2-propanol), propranolol (1-[(1-methylethyl)amino]-3-(1-naphthalenyloxy)-2-propanol), timolol (1-[(1,1-dimethylethyl)amino]-3-[(4-morpholinyl-1,2,5-thiadiazol-3-yl)oxy]-2-propanol), labetalol (2-hydroxy-5-[1-hydroxy-2-[(1-methyl-3-phenylpropyl)amino]ethyl]-benzamide), betaxolol (1-[4-[2-(cyclopropylmethoxy)ethyl]-phenoxy]-3 -[(methylethyl)amino]-2-propanol), carteolol (5-[3-[(1,1dimethylethyl)amino]-2-hydroxypropoxy]-3,4-dihydro-2(1H)-quinolinone), and dilevalol ([R-(R,R)]-2-hydroxy-5-[1-hydroxy-2-[(1-methyl-3-phenylpropyl)amino]ethyl]-benzamide 4-methylbenzenesulfonate salt), "and pharmaceutically acceptable salts and isomers thereof".

The usefulness of beta adrenergic blockers for lowering intraocular pressure is known in the art. Thus, the beta adrenergic blocker timolol, is currently approved by the U.S. Food and Drug Administration for topical use as a treatment for glaucoma. It is marketed in two dose strengths, i.e., 0.25% and 0.5%. As previously stated, this agent must be used with caution in a defined patient population because of recognized untoward side effects (see Physicians Desk Reference for Ophthalmology, 11th edition, 1983, p. 126, Medical Economics Co. Inc., Oradell, N.J. 07649).

As one aspect of the present invention, it is contemplated that a reduction in intraocular pressure equivalent to that obtained by use of a beta-blocker, e.g., the approved clinical dose of the beta-blocker timolol, may be obtained by use of a lower dose of beta-blocker when such lower dose is combined with an effective amount of a compound of formula I. It is anticipated that the use of the diminished dosage of beta-blocker, e.g., timolol, will result in a reduction of severity and frequency of timolol-like related side effects.

For purposes of this combination treatment modality, the beta-blocker and compound of formula I are preferably administered simultaneously as one composition in one pharmaceutical dosage form, but they may be applied as separate topical compositions, if desired. When applied as part of a composition including a compound of formula I, the beta adrenergic blocker may comprise from about 0.01% to about 1.0% of the composition of the invention. The preferred ranges of the components in the composition of the invention in unit dosage form are as follows:

Beta adrenergic blocker: from 5 μg to 250 μg
Compound of formula I: from 5 ng to 5 μg.

When applied in separate compositions, the beta-adrenergic blocker and compound of formula I may be included in such compositions in the same ranges. The individual dosage requirements, i.e., the amount of each dose and the frequency of administration, may vary depending on the severity of the disease and the response of the patient.

Since the composition of the invention and the composition including the beta-adrenergic blocker can be administered separately, the invention also relates to combining separate pharmaceutical compositions in kit form, that is, combining two separate units, an inventive pharmaceutical composition and a topical pharmaceutical composition including a beta-adrenergic blocker, in a single package. A particular advantage of the kit resides in the ability to provide a combination of an inventive composition which can be administered once or twice a day and a topical beta-adrenergic blocker composition which may be administered as necessary or desired.

Those skilled in the art will appreciate that the "intraocular pressure reducing concentration" for such combination therapy will consist of a range of concentrations (doses), and that there will be a lower limit to said concentration below which, the present invention will not operate. For purposes of this invention, this lower limit or minimum dosage may be considered to be about 5% of the effective dose (threshold dose) of the particular component. The intraocular pressure reducing concentration that is actually utilized, whether for a compound defined in formula I or for a particular beta adrenergic blocker, will depend on, inter alia, the potency of each particular material, the combination being administered and the age, size and condition of the patient being treated as well as on the severity of the disease state.

We also contemplate that the elevation in IOP associated with the clinical ophthalmic and systemic use of anti-inflammatory steroids can be reduced by the administration of a composition of the present invention. In particular, an increase in IOP is most often associated with the administration of steroidal anti-inflammatory agents. Anti-inflammatory steroids include hydrocortisone, cortisone, prednisolone, orednisone, dexamethasone, methylprednisolone, triamcinolone, betamethasone, alclometasone, flunisolide, beclomethasone, clorocortolone, diflorasone, halcinonide, fluocinonide, flucinolone, desoximetasone, medrysone, parametasone, 9,21-dichloro-17-[(2-furanylcarbonyl)oxy]-11-hydroxy-16α-methyl-pregna-1,4-diene-3,20-dione and fluorometholone, and their pharmaceutically acceptable salts and esters. Preferred steroids are hydrocortisone, prednisolone, dexamethasone, betamethasone, beclomethasone, medrysone and fluoromethalone and their pharmaceutically acceptable salts and esters. This rise in IOP may occur with all modes of administration of the drugs, including systemic (usually oral), local injection (e.g., depot injection), and especially with ophthalmic topical or intravitreal administration. The composition of the present invention may be administered following steroid treatment to lower elevated IOP, or may be co-administered with the steroid to suppress the IOP-raising effect of the steroid while not interfering with the anti-inflammatory activity of the steroid.

It is further contemplated that any possible combination of dosage forms may be used to administer the combination, e.g., oral steroid/topical composition of the invention, topical steroid/oral composition of the invention, oral steroid/oral composition of the invention, topical steroid/topical composition of the invention, and locally injected steroid/topical composition of the invention, although a preferred combination comprises a steroid and a topical composition of the invention. For ophthalmic use, a combination of a topical steroid and a topical composition of the invention is preferred. More preferred is a topical ophthalmic pharmaceutical dosage form comprising both a steroid and a composition of the invention. Such compositions or combinations can be employed in a method for reducing and controlling the elevated IOP associated with ophthalmic and systemic use of steroidal anti-inflammatory agents, which method comprises administering to a mammal effective amounts of a steroid and a composition of the invention, either separately or in the same pharmaceutical composition.

Since the present invention relates to treatment with a combination of a composition of the invention and a steroidal anti-inflammatory agent wherein the inventive composition and steroid may be administered separately, the invention also relates to combining separate pharmaceutical compositions in kit form, that is, combining two separate units, an inventive pharmaceutical composition and a steroid pharmaceutical composition, in a single package. Preferred components of the kit comprise a topical opthamological pharmaceutical composition including a compound of formula I and a pharmaceutically acceptable steroid composition. More preferred components of the kit are a topical opthamological inventive pharmaceutical composition including a compound of formula I and a topical opthamological steroid pharmaceutical composition. A particular advantage of the more preferred embodiment of the kit resides in the ability to provide a combination of an inventive composition which can be administered once or twice a day and a steroid composition which may be administered as frequently as once each hour.

In this combination treatment modality, topical formulations of the invention may combine the following amounts of each inventive composition and steroidal constituent, or each constituent may be administered separately:

A compound of formula I from about 0.000001% (w/v) to about 1.0% and especially about 0.00001% to about 0.01% of medicament. As a unit dosage form, an amount of a compound of formula I from about 0.5 ng to about 0.5 mg preferably about 5 ng to about 5 $\mu$g, of the active component is applied to the human eye. Individual dosage requirements, i.e., the amount of each dose and the frequency of administration, will depend on the potency of the particular composition of the invention, the severity of the increase in IOP and the response of the patient.

Steroid from about 0.05 to about 1.5 (w/v %) of medicament. As a unit dosage form, an amount of steroid from between 20 $\mu$g to 600 $\mu$g of the active composition is applied to the human eye. Individual dosage requirements, i.e., the amount of each dose and the frequency of administration will depend on the potency of the particular steroid, the severity of the disease and the response of the patient. Approximate ranges for such steroids are well known to those skilled in the art. The particular steroid selected will determine which inventive composition and concentration thereof to select for use in a combination preparation.

In one embodiment of the invention, both active ingredients, i.e., inventive composition and steroid, will be administered simultaneously and be contained in one pharmaceutical dosage form, each component being present in the dosage form in its own respective preferred concentration. When the steroid is administered systemically or topically other than in an ophthalmological composition, the concentration of the steroid in the composition and the unit dosage weight may vary considerably, depending as above on such factors as the potency of the steroid, its onset and duration of action as well as the severity of the disease, and the response of the patient. Appropriate dosage ranges for systemic and topical administration of each steroid are well known in the art.

Those skilled in the art will know that for solutions and suspensions, a particular dosage of active ingredient may be calculated if one assumes that one drop of solution is being administered and if one knows the concentration (w/v) of the particular solution that is being administered. Thus, one drop (1/20 ml) of a 0.25% solution (contains 2.5 mg of active per ml) is known to contain .125 mg or 125 $\mu$g of active ingredient.

The IOP-lowering effects of the compositions employed in the invention may be measured by the procedure described by Watkins et al., J. Ocular Pharmacol. 1 (2):161-168, 1985.

The following procedures and examples illustrate the preparation of compounds employed in this invention.

PREPARATION 1 t-BUTYL 2(S)-(TRIFLUOROMETHANESULFONYLOXY)-PROPRIONATE (Triflate Reagent)

A. Add 2(S)-(p-toluenesulfonyloxy)propionic acid (4.4 g) to a cold solution of 10ml of isobutylene and 0.4 ml of concentrated sulfuric acid in 30 ml of methylene chloride in a pressure vessel, seal, and agitate at room temperature for 48 hours. Pour into 50 ml of 15% sodium carbonate solution, dry over magnesium sulfate and concentrate to obtain t-butyl 2(S)-(p-toluenesulfonyloxy)propionate as an oil (NMR $\delta$ 1.37). Distilled material (Kugelrohr, 120°) has $[\alpha]D^{26} = -45.9°$ (EtOH, c=1).

B. Combine the product of part A (100 g) with acetic acid (40.0 g) and triethylamine (67.2 g) in 200 ml of dry DMF. Heat at 65° for 20 hours. Partition with 21 each ether and water, and wash the ether with citric acid, then with dilute sodium bicarbonate solution. Dry and concentrate the ether solution to obtain t-butyl 2(R)-acetoxypropionate as a colorless liquid, bp 50° C./0.1 mm.

C. Combine the product of part B (62,6 g) with ethylenediamine (11.6 g) and heat at 70° for 24 hours. allow to cool, add 300 ml ether and filter. Wash the ether with water, 10% citric acid, and then with sodium bicarbonate solution. Dry and concentrate the ether solution to leave a colorless oil. Crystallize from hexane at −20° to give t-butyl 2(R])-hydroxypropionate as white needles, m.p. 41°-2° C.

D. Combine the product of part C (10 g) with pyridine (6 ml) in 100ml methylene chloride. Cool to −70° C., and add dropwise over a period of about 45 minutes a solution of trifluoromethanesulfonic anhydride (13.5 g) in 20 ml methylene chloride, maintaining the temperature below −15° C. Stir at −20° C. for 30 min. Add ether and wash successively with water, 4 of aq HCl, sat'd NaHCO$_3$ and brine. Dry and concentrate the organic layer to obtain the title compound.

PREPARATION 2

6-CHLORO-3,4-DIHYDRO-3-(2-PHENYLETHYL)-2H-1,2,4-BENZOTHIADIAZINE-7-SULFONYL CHLORIDE 1,1-DIOXIDE

A. Dissolve 5 g 2-chloroaniline-3,5-disulphonyl chloride in 20 ml DME, cool to in a dry-ice/acetone both and add 2 ml triethylamine.

Add dropwise 25% ammonium hydroxide in water (1 ml) in DME (4 ml), stir at in a dry-ice acetone bath for 1 hour, allow to warm to room temperature, and stir for 90 min. Dilute the resultant reaction mixture with ethyl acetate, wash with 4% ac HCl, water and brine, dry over MgSO$_4$ and evaporate to obtain a solid residue.

B. Combine 13.6 g of the sulfonamide prepared in Step A, 6.57 g phenyl propanal, 25 ml DME and 20 mg p-tolulenesulfonic acid and stir at room temperature under N$_2$ for 3 hours. Evaporate the solvent, dissolve the resultant residue in 250 ml ethyl acetate, wash with 100 ml sat'd aq. NaHCO$_3$, and 100 ml brine, then dry over MgSO$_4$, filter and evaporate the solvent to obtain the crude title compound. Purify the crude residue by precipitation in CH$_2$Cl$_2$; mp. 167.0°–167.5° C.

PREPARATION 3

CIS,SYN-OCTAHYDROINDOLE-2(S)-CARBOXYLIC ACID, t-BUTYL ESTER

A. Dissolve the product of Preparation 4 (77 g) in absolute ethanol (900 ml), add 5% Pd/C (10 g) and hydrogenate at room temperature at an initial pressure of 60 p.s.i. After 3 hours, filter off the catalyst and wash with hot methanol. Evaporate the combined filtrate and wash in vacuo, triturate the resultant residue in ethanol (100 ml), chill the solution, then filter and air dry the resultant precipitate to obtain a residue, m.p. 269°–270° C.

B. Suspend the product of Part A in dioxane (400 ml) and conc. H$_2$SO$_4$ (40 ml), add isobutylene (300 ml) and shake in a Parr shaker for 28 hours. Pour the resultant reaction mixture into 50% aqueous NaOH (150 ml) in 500 ml ice water and extract with ethyl ether (3×500 ml). Wash the combined organic extracts with water, then brine. Dry the organic layer over Na$_2$SO$_4$ and evaporate the solvent to obtain the title compound.

PREPARATION 4

CIS,SYN-OCTAHYDROINDOLE-2(S)-CARBOXYLIC ACID BENZYL ESTER

A. Dissolve 27.0 g of ethyl indole-2-carboxylate in 250 ml of trifluoroacetic acid. Add 2.05 g of platinum oxide, hydrogenate the mixture at 50 lb/in$^2$ at room temperature. Filter the mixture and concentrate the filtrate in vacuo to give a residue. Suspend the residue in ether and treat with cold dilute sodium hydroxide solution. Dry the organic layer over magnesium sulfate and concentrate it to give ethyl octahydroindole-2-carboxylate, a pale yellow oil.

B. Dissolve 116 g 10-d-camphorsulfonic acid in 1 liter of warm ethyl acetate and add a solution of 86 g of the product of part A in 1 liter of ethyl acetate. Allow the mixture to crystalline, heat to reflux, cool to room temperature, and filter. Recrystallize the filter cake from a mixture of 500 ml isopropanol and 1800 ml ethyl acetate, filter and dry the crystals to obtain 2-(S)-carboethoxy-cys,syn-octahydroindole, d-10-camphorsulfonate, m.p. 192°–193° C.

C. Heat the product of Part B (107.6 g) and d-10-camphor-sulfonic acid (6.35 g) in benzyl alcohol (270 ml) at 105° C. under vacuum for 6 hours or until TLC (silica, elute neutralize sample with ethyl ether) indicates reaction is complete. Pour the resultant residue into ethyl ether, seed and stir to obtain a precipitate. Filter the precipitate, wash with ethyl ether (2×500 ml) and dry the resultant residue under vacuum to obtain 2-(S)-benzyloxy-cis, syn-octahydro-indole, d-10-camphorsulfonate, m.p. 114°–118° C.

D. Suspend the product of Part C (150 g) in ethyl ether (1500 ml), add 1 N aqueous NaOH (300 ml) and stir until the solid dissolves. Separate the organic layer and wash the aqueous layer with ethyl ether (2×200 ml). Combine the organic layer, wash with brine, dry over Na$_2$SO$_4$ and evaporate the solvent to obtain the title compound.

PREPARATION 5

6-CHLORO-3,4-DIHYDRO-3—(CHLOROMETHYL)-2H-1,2,4-BENZOTHIADIAZINE-7-SULFONYL CHLORIDE 1,1-DIOXIDE

A. Dissolve the sulfonamide prepared in Part A of Preparation 2 (20 g) in dry DME (100 ml), add chloroacetaldehyde dimethyl acetal (10 ml) and p-toluenesulfonic acid and reflux for 3 hours or until TLC (silica, 3% ethyl acetate in CH$_2$Cl$_2$) indicates reaction is complete. Evaporate the solvent, dissolve the resultant residue in ethyl acetate, wash with saturated NaHCO$_3$, then brine and concentrate to half volume. Refrigerate overnight, filter the resultant precipitate, wash in hexane, filter and dry to obtain the title compound.

EXAMPLE 1

1-[2-(S)-[[1-(S)-CARBOETHOXY-2-[4-[[[6-CHLORO-3,4-DIHYDRO-3-(2-PHENYLETHYL)-2H-1,2,4-BENZOTHIADIAZIN-7YL]SULFONYLAMINO]-METHYL]PHENYLMETHOXY]ETHYL]AMINO]-1 OXOPROPYL]-[2S-[2α, 3aα, 7aα]]-OCTAHYDRO-1H-INDOLE-2-CARBOXYLIC ACID, S,S-DIOXIDE

A. To 10.4 g NaH (50% in mineral oil, washed with hexane) in 50 ml DMF at 0°–5° C., add dropwise over a 1 hour period 20o of N-a-t-butoxycarbonyl-L-serine in 350 ml DMF. Stir at room temperature for 1 hour, then at 45° for 1 hour. Cool the reaction mixture to 0°–5° C. and add dropwise over 30 minutes 21.3 g of p-cyanobenzylbromide in 100 ml DMF. Stir at 0° C. for 80 minutes, add 30 ml water, stir and filter. Concentrate the filtrate and partition between ethyl acetate and sat'd. aq. NaHCO$_3$/H$_2$O. Wash the aqueous phase with ethyl acetate, adjust to pH 7.5 with 6 N HCl and concentrate to approximately 100 mls.

B. To the product of Step A, add 60 ml methanol, 40 ml ethyliodide, and 4 g NaHCO$_3$. Stir under a nitrogen atmosphere for 72 hours, evaporate the solvent in vacuo and partition the residue between 800 ml ethyl acetate and 800 ml water. Separate the organic layer, and extract the aqueous layer with ethyl acetate; combine the organic extracts, wash with brine, dry over MgSO$_4$, filter and evaporate the solvent. Purify the resultant residue by High Pressure Liquid Chromatography (HPLC) using 2 Prep 500 cartridges and eluting with 21% ethyl acetate in hexane. Combine the desired fractions and evaporate the solvent to obtain a residue. FAB mass spec m/e=349 (M+H).

C. Cool 2 g of the product of Step B to 0°–5° C. and add dropwise 25 ml of trifluoroacetic acid. Let stand until TLC (silica, elute with hexane:ethyl acetate) indicates no starting material is left. Add ethyl acetate, then evaporate the solvent in vacuo. Dissolve the resultant residue in ethyl ether, and wash with 1 N aqueous NaOH; backwash the aqueous phase with ether, combine the ethereal extracts, dry over K$_2$CO$_3$ and evaporate the solvent to obtain a residue.

D. Cool 1.6 g triflate reagent (Preparation 1) in 10 ml CH$_2$Cl$_2$ to 0° C. Add dropwise 1.1 g of the product of Step C and 1.2 g of PROTON SPONGE® (1,8-bis(-dimethylamino)naphthalene, Aldrich Chemical Co., Milwaukee, Wis.) in 20 ml CH$_2$Cl$_2$. Monitor reaction by TLC, adding 1,8-bis-(dimethylamino)naphthalene and triflate reagent as necessary. Filter the resultant precipitate with the aid of ethyl acetate, evaporate the solvent, and purify the resultant residue by column chromatography, eluting with 30% ethyl acetate in hexane. FAB mass spec m/e=377 (M+H).

E. Dissolve 2.5 g of the product of Step D in 50 ml ethanol saturated with $NH_3$, add 1.25 g 5% $Rh/Al_2O_3$ and hydrogenate at 60 psi for 4 hours. Filter the resultant mixture through celite with the aid of ethanol, then evaporate the solvent in vacuo to obtain a residue.

F. Cool to 0° C. 2.5 g of the product of Step E in 25 ml dry THF and add dropwise 3.3 g 6-chloro-3,4-dihydro-3-(2-phenylethyl)-2H-1,2,4-benzothiadiazine-7-sulfonyl chloride 1,1-dioxide in 20 ml dry THF. Stir at 0° C. for 1 hour, then add 0.6 ml N,N-diisopropylethylamine and stir at room temperature for 2 hours. (Reaction may be monitored by TLC [silica; elute with hexane: ethyl acetate]). Add the reaction mixture to ethyl acetate, wash with 4% aq. HCl, sat'd $NaHCO_3$ and brine, then dry over $MgSO_4$ and evaporate the solvent in vacuo. Purify the resultant residue by HPLC: dissolve the residue in acetone:ethyl acetate:hexane (20:35:45) and separate on 2 Prep 500 cartridges using acetone:ethyl acetate:hexane (5.5:36.5:58) as mobile phase. Monitor eluent by TLC (silica; elute with acetone:ethyl acetate:hexane [6:39:55]), combine the desired fractions and evaporate the solvent in vacuo to obtain a residue. FAB mass spec m/e=766 (M+H).

G. Stir 2.9 g of the t-butyl ester of Step F in 40 ml HCl/dioxane overnight; pass nitrogen through the solution to evaporate the solvent and obtain the free acid.

H. Dissolve 2.9 g of the produce of Step G in 6 ml DMF, add 1.1 g cis,syn-octahydro-1H-indole-2(S)carboxylic acid, t-butyl ester and 700 mg 1-hydroxybenzotriazole. Cool to 0° C., add 0.7 ml triethylamine and 900 mg 1-(3-dimethylaminopropyl)-3-ethyl carboiimide hydrochloride and stir overnight. Evaporate the solvent in vacuo, take up the residue in ethyl acetate, and wash with water, 4% aq. HCl, sat'd aq. $NaHCO_3$, and brine. Dry the organic layer over $MgSO_4$, filter and evaporate to obtain a residue.

Purify said residue by HPLC using 2 Prep 500 cartridges and methanol:ethyl acetate:hexane (5.25:36:58.75) as mobile phase (residue dissolved in methanol:ethyl acetate:hexane [10:35:55]). Combine the desired fractions as determined by TLC and evaporate the solvent. Rechromatograph the resultant residue by HPLC using aceone:ethylacetate:hexane (10:40:50) as mobile phase, combining the desired fractions and evaporating the solvent to yield the title compound as a t-butyl ester. FAB mass spec m/e=917 (M+H).

I. Stir 1.5 g of the product of Step H in 20 ml dioxane saturated with HCl overnight; pass nitrogen through the solution to evaporate the solvent. Purify the resultant residue on Dowex Ag 50 2X (H+ form), eluting with (ethanol:water [1:1]):pyridine (95:5). Combine desired fractions as determined by TLC (silica; $CH_2Cl_2$:MeoH:AcOH [90:5:3]) and evaporate the solvent to obtain the title compound. FAB mass spec m/e=861 (M+H).

EXAMPLE 2

1-[2-(S)-[[1-(S)-CARBOXY-2-[4-[[[6-CHLORO-3,4-DIHYDRO-3-(2-PHENYLETHYL)-2H-1,2,4-BENZOTHIADIAZIN-7-YL]SULFONYLAMINO]METHYL]PHEYLMETHOXY]ETHYL]AMINO]-1 OXOPROPYL]-[2S-(2α, 3aα, 7aα)]-OCTAHYDRO-1H-INDOLE-2-CARBOXYLIC ACID, S,S-DIXOIDE.

A. Treat the produce of Example 1, Step G in a manner similar to that described in Example 1, Step H, first paragraph, substituting cis,syn-octahydro-1H-indole-2(S)-carboxylic acid, benzyl ester camphorsulfonate salt (see Preparation 4, part C) for the t-butyl ester.

Purify the resultant residue by column chromatography on 100 g silica eluted with $CHCl_3$:ethyl acetate. Combine the desired fractions as determined by TLC (silica; elute with $CH_2Cl_2$:methanol:acetone [93:2:5]) and evaporate the solvent to obtain a residue. Further purify the residue on a sephadex column (350 g). FAB mass spec m/e=951 (M+H).

B. Suspend 450 mg of the diester obtained in Step A in 2 ml water. Add 2 ml 1 N aq. NaOH and stir overnight at room temperature. Adjust to pH 6-7 with 1 N HCl, filter the resultant solid and dry under vacuum to obtain the title compound. FAB mass spec m/e=833 (M+H).

EXAMPLE 3

1-[2-(S)-[[3-[4-[[[6-CHLORO-3,4-DIHYDRO-3-(2-PHENYLETHYL)-2H-1,2,4-BENZOTHIADIAZIN-7-YL]SULFONYLAMINOMETHYL]PHENYL]-1-(S)-(ETHOXYCARBONYL)PROPYL]AMINO]-1OXOPROPYL]-[2S-(2α, 3aα, 7aα]-OCTAHYDRO-1H-INDOLE-2-CARBOXYLIC ACID, S,S -DIOXIDE HYDROCHLORIDE

A. 2-Amino-4-(4-cyano)phenylbutanoic acid, ethyl ester

Reflux 2-(4-cyano)phenylethyl bromide (23 gm), the p-chlorobenzaldimine of ethyl glycinate (21 gm), tetra-n-butylammonium bromide (10 oms) and freshly ground fine potassium carbonate powder (42 gms) in acetonitrile (150 mls) with mechanical stirring under nitrogen for 12 hours.

Cool the mixture, filter off the solid and wash the filter cake with ethyl acetate (3×150 mls). Wash the combined filtrate with water (2×100 mls) and evaporate the solvent in vacuo. Stir the residue vigorously with THF (200 mls) and 2 N HCl (200 mls) at room temperature for 2 hours. Wash the aqueous phase with ethyl acetate, basify with solid potassium carbonate to pH 9 and extract with ethyl acetate to give the title compound of Part A.

B.
N-[1-(S)-(Ethoxycarbonyl)-3-(4-cyano)phenyl]-(S)-alanine, t-butyl ester

Slowly add the product of Part A (9 gms) and PROTON SPONGE® (17.2 gm) in dry dichloromethane (80 mls) dropwise into a stirred solution of triflate reagent (22 gm) in dry dichloromethane (40 mls) cooled in an acetone-ice bath. Stir at room temperature overnight. Filter the resultant precipitate and wash the filter cake with ethyl acetate (5×100 ml). Wash the combined filtrate with 10% citric acid (3×100 ml); sodium bicarbonate (sat'd, 2×100 ml), and saturated brine (2×100 ml). Dry the solution over potassium carbonate in the presence of triethyl amine (5 mls), and remove the solvent in vacuo. Chromatograph the resultant residue (hexane:EtOAc:CH$_2$Cl$_2$ [8:1:1], 1% Et$_3$N; 500 gm silica gel; 230–400 mesh) to obtain the title compound of Part B.

C.

N-[3-(4-Aminomethyl)phenyl-1-(S)-(ethoxycarbonyl) propyl]-(S)-alanine, t-butyl ester Hydrogenate a mixture of the product of Part B (2 g), hydrogen chloride (0.2 gm) and 10% Pd/C (0.4 gm) in absolute ethanol (100 ml) at 50 psi for 5 hours. Filter the resultant mixture through celite. Evaporate the solvent to obtain the hydrogen chloride salt of the title compound of Part C.

D. Add N-methylmorpholine (0.5 ml) to a solution of the product of Part C (1 gm) in dry THF (20 mls) cooled in acetone-ice bath (−5° C). Add the sulfonyl chloride of Preparation 2 (1.3 gm) and stir the resulting mixture at room temperature overnight. Dilute the resultant reaction mixture with ethyl acetate (400 ml), wash with 0.5 N HCl (100 ml), saturated NaHHCO$_3$ (2×100 ml), and brine (2×100 ml). Dry the solution over MgSO$_4$ and remove the solvent in vacuo. Purify the resultant residue by chromatography [400 gm silica gel, 230–400 mesh; first hexane:EtOAc:CH$_2$Cl$_2$, 4:1:1, then hexane:EtOAc:CH$_2$Cl$_2$, 1:1:1] to obtain a residue.

E. Add the product of Part D (1.76 gm) to 5.5 M HCl in dioxane (50 ml) and stir the resulting mixture at room temperature overnight. Evaporate the solvent in vacuo, triturate the solid residue with ether, and remove the solvent in vacuo to obtain a residue (hydrogen chloride salt).

F. Treat the product of part E in a manner similar to that described in Example 1, Part H, first paragraph, substituting N-methylmorpholine for triethylamine to obtain a residue. Purify the resultant residue by chromatography [400 gm silica gel 230–400 mesh; hexane:EtOAc:CH$_2$Cl$_2$, 1:2:1] to obtain the t-butyl ester of the title compound.

G. Stir the product of Part F (0.9 gm) in 5.5 M HCl/dioxane (40 mls) at room temperature for 2 hours. Remove the solvent in vacuo, triturate the product with ether, and dry in vacuo to obtain the title compound of Example 3.

EXAMPLE 4

1-[2-(S)-[[1-(S)-CARBOXY-3-[4-[[[6--CHLORO-3,4-DIHYDRO-3-(2-PHENYLETHYL)-2H-1,2,4-BENZOTHIADIAZIN-7-YL]SULFONYLAMINO]METHYL]PHENYL]-PROPYL]AMINO]-1-OXOPROPYL]-[2S-(2α,3aα,7aα)]-OCTAHYDRO-1H-INDOLE-2-CARBOXYLIC ACID, S,S- DIOXIDE

Dissolve the product of Example 3 (0.85 gm) in methanol (2 mls) and cool to 0° C under nitrogen. Add 1 N sodium hydroxide (5 mls) portionwise. Refrigerate the mixture overnight. Acidify the resultant mixture with acetic acid, evaporate to dryness, and purify the residue by chromatography on a C-18 medium pressure reverse-phase column to yield the title compound of Example 4.

EXAMPLE 5

1-[[2-(S)-[5-[[6-CHLORO-3-CHLOROMETHYL-3,4-DIHYDRO-2H-1,2,4-BENZOTHIADIAZIN-7-YL]SULFONYLAMINO]-1-(S)-(ETHOXYCARBONYL)PENTYL]AMINO]-1-OXOPROPYL]-[2S-(2α,3aα,7aα)]-OCTAHYDRO-1H-INDOLE-2-CARBOXYLIC ACID, S,S-DIOXIDE

A. Combine N$^\epsilon$Cbz lysine, ethyl ester (30.0 g), t-butyl bromopropionate (44.78 g), triethylamine (14.8 ml) and DMF (120 ml) and stir under nitrogen at 75° C until TLC shows no starting material present. Evaporate the solvent, dilute the resultant residue with water and extract with ethyl ether. Wash the organic layer with brine, dry over MgSO$_4$, filter and evaporate the solvent in vacuo.

Purify the resultant residue by column chromatography on 1,100 g silica gel (60–200 mesh), eluting with ether:hexane (50:50.75:50). Combine the desired fractions and evaporate the solvent in air. Further purify the resultant residue by HPLC using 2 Prep 500 cartridges and eluting with ether:hexane. Combine desired fractions, dry over MgSO$_4$ and evaporate the solvent in air to obtain a residue.

B. Combine 20% Pd(OH)$_2$/C (21.1 g) and anhydrous ethanol (25 ml) in a Parr shaker bottle, add the product of Part A (16.5 g) in ethanol (55 ml) and hydrogenate overnight under 60 p.s.i. H$_2$. Filter the resultant solution over filter paper and celite and evaporate the solvent to obtain a residue.

C. Dissolve the sulfonyl chloride prepared in Preparation 5 (2.4 g) in dry DME (15 ml). Add triethylamine (1 ml) and the product of Part B of this Example (2 g) in DMF (10 ml) and stir for 1 hour, or until TLC (silica, 10% MeOH in CH$_2$Cl$_2$) indicates no starting material is left. Add the resultant solution to ethyl acetate, wash with water, saturated NaHHCO$_3$ and brine, dry over MgSO$_4$ and evaporate the solvent in vacuo. Purify the resultant residue on a Sephadex LH20 column to obtain a residue. FAB mass spec m/e=632 (M+H).

D. Treat the product of Part C in a manner similar to that described in Example 1, Part G.

E. Treat the product of Part D in a manner similar to that described in Example 1, Part H, first paragraph, substituting the camphorsulfonate salt of the benzyl ester of the octahydroindole (see Preparation 4 Part C) for the t-butyl ester.

Purify the resultant residue on a sephadex LH20 column, combine the desired fractions and evaporate the solvent. Dissolve the resultant residue in ethyl acetate, add dioxane saturated with HCl and evaporate the solvent to obtain the benzyl ester of the title compound. FAB mass spec m/e=817 (M+H).

F. Dissolve the product of Part E (600 mg) in acetic acid saturated with hydrogen bromide (6 ml). After 5 hours, evaporate the solvent and purify the resultant residue on a Sephadex LH20 column. Combine the desired fractions as determined by TLC (silica, MeOH:CH$_2$Cl$_2$:acetic acid, 10:90:4) and evaporate the solvent to obtain the title compound. FAB mass spec m/e=726 (M+H).

EXAMPLE 6

1-[[2-(S)-[1-(S)-CARBOXY-5-[[6-CHLORO-3-CHLOROMETHYL-3,4-DIHYDRO-2H-1,2,4-BENZOTHIADIAZIN-7-YL]SULFONYLAMINO]-PENTYL]AMINO]-1-OXOPROPYL]-[2S-(2α,3aα,7aα)]-OCTAHYDRO-1H-INDOLE-2-CARBOXYLIC ACID, S,S-DIOXIDE

Add the product of Example 5, Part E (benzyl ester) to 1 N aqueous NaOH (4 ml) and water (4 ml) and stir overnight. Add 1 N HCl (4 ml) and ethanol. Charge the resultant solution to Dowex Ag 50 cation exchange resin by stirring batchwise for 20 minutes (60 ml resin, pre-washed with ethanol:water, 1:4). Prepare a column from the loaded resin, elute the column with ethanol:water (1:4) until the elute is pH 6, then elute with ethanol/water:pyridine (95:5). Combine the desired fractions as determined by TLC (silica, ethanol:water, 9:1). Further purify the resultant product on a Sephadex LH 20 column. Combine the desired fractions and evaporate the solvent to obtain the title compound. FAB mass spec m/e+698 (M+H).

EXAMPLE 7

N-[2-[[4-[[[6-CHLORO-3,4-DIHYDRO-3-(2-PHENYLETHYL)-2H-1,2,4-BENZOTHIADIAZIN-7-YL]SULFONYLAMINO]METHYL]PHENYL]-CARBONYL]AMINO-1-(S)-(ETHOXYCARBONYL)ETHYL]-(S)-ALANYL-(S)-PROLINE, S,S-DIOXIDE

A. Dissolve 4-cyanobenzoic acid, t-butyl ester (11.34 g) in ethanol (100 ml) saturated with anhydrous NH$_3$, add 5% Rh/Al$_2$O$_3$ (120 g) and hydrogenate in a Parr apparatus at 60 p.s.i. at room temperature for 2¾ hours. Filter the resultant solution through celite and evaporate the solvent to obtain a residue.

B. Dissolve the product of Part A (11.27 g) in dry THF (100 ml) add N,N,-diisopropylethyl amine (8.44 g) and cool to 0° C. in an ice bath. Add dropwise, slowly and with stirring, the sulfonyl chloride prepared in Preparation 2 (27.51 g) and let stand at 0° C. for 35 minutes. Remove the ice bath and stir at room temperature for 2 ½ hours or until TLC (silica, CH$_2$Cl$_2$:MeOH, 95:5) shows the reaction to be complete Evaporate the solvent to obtain a residue.

C. Cool to 0° C. a solution of the product of Part B (3.00 g) in CH$_2$Cl$_2$ (25 ml) and add, slowly and with stirring, trifluoroacetic acid (25 ml). Stir for 30 minutes at 0° C., then at room temperature for 2½ hours or until TLC (as in Part B) shows the reaction to be complete. Evaporate the solvent to obtain a residue.

D. Dissolve triflate reagent as prepared in Preparation 1 (3.31 g) in CH$_2$Cl$_2$ (75 ml) and cool to 0° C.; add, slowly and with stirring a solution of PROTON SPONGE® (4.24 g) and N-βCbz-2,3-diaminopropionate, ethyl ester (2.00 g) in CH$_2$Cl$_2$ (75 ml). Stir at 0° C. for 15 hours. Extract the solution with 10% citric acid (2×), then sat'd. NaHHCO$_3$ (2×), dry the organic layer over MgSO$_4$, filter and evaporate the solvent. Purify the resultant residue by flash chromatography, eluting with CH$_2$Cl$_2$:EtOAc (88:12). Combine the desired fractions and evaporate the solvent. Dissolve the Cbz-diester (0.5 g) in ethanol (25 ml) containing 20% Pd(OH)$_2$/C (0.15 g) and hydrogenate in a Parr apparatus at 50 p.s.i. at room temperature for 1 hour. Filter the resultant solution through celite and evaporate the filtrate in vacuo.

Combine the resultant residue (0.33 g) and the product of Part C (0.59 g) in dry DMF (7 ml), cool to 0° C. and add slowly 1-hydroxybenzotriazole (0.18 g) followed by N-methyl morpholine (0.13 g), then by DEC (0.25 g). Stir the mixture for 20 min. at 0° C., then at room temperature for 16 hours or until TLC (silica, ethanol:methanol, 85:15) indicates the reaction to be complete. Dilute the reaction mixture with CH$_2$Cl$_2$ and extract with saturated NaHHCO$_3$, then with 10% aqueous citric acid. Dry the organic layer with MgSO$_4$, filter and evaporate the solvent in vacuo to obtain a residue.

E. Dissolve the product of Part D (0.75 g) in CH$_2$Cl$_2$ (5 ml) and cool to 0° C. Add, slowly and with stirring, trifluoroacetic acid (5 ml) and stir at 0° C. for 30 minutes, then at room temperature for 4 hours or until TLC (silica, CH$_2$Cl$_2$:MeOH, 90:10) indicates no starting material is left. Evaporate the solvent.

Purify the resultant residue by ion exchange chromatography on Biorad AG50-W-X2 resin (100–200 mesh, hydrogen form) previously equilibrated in ethanol:water. Elute with ethanol:water:pyridine, combine the desired fractions and evaporate the solvent to obtain a residue.

F. Treat the product of Part E in a manner similar to that described in Example 3, Parts F and G, substituting proline, t-butyl ester for the octahydro-1H-indole to obtain the title compound.

EXAMPLE 8

N-[5-[[6-CHLORO-3,4-DIHYDRO-3-(2-PHENYLETHYL)-2H-1,2,4-BENZOTHIADIAZIN-7-YL]SULFONYLAMINO]-1-(S)-(METHOXYCARBONYL)PENTYN-3-YL]-(S)-ALANYL-(S)-PROLINE, S,S-DIOXIDE,HYDROCHLORIDE

A. Titrate a solution of diazomethane in ether into a solution of 1-amino-1-(S)-carboxy-5-(t-butoxycarbonyl amino)-3-pentyne (4 g) in ethanol (200 ml) until a yellow color remains. Evaporate the solvent to obtain 1-amino-1-(s)-methoxycarbonyl-5-(t-butoxycarbonylamino)-3pentyne.

B. Add the product of Part A (4 g) and PROTON SPONGE® (5 g) in dichloromethane (15 ml) dropwise to a stirred solution of triflate reagent (6.5 g) (See Preparation 1) in dichloromethane (10 ml) at −10° C. Stir the solution and slowly allow to warm to room temperature over 2 h. Filter the reaction mixture through celite, washing thoroughly with ethyl acetate. Wash the combined organic solution with 10% citric acid (3×), saturated sodium bicarbonate (2×) and brine (2×), dry over MgSO$_4$ and evaporate the solvent. Chromatograph on silica gel, eluting with ethyl acetate:hexane (1:4) containing 1% triethylamine to obtain 1-(S)-methoxycarbonyl-5-(t-butoxycarbonylamino)pentyn-3-yl-(S)-alanine, t-butyl ester.

C. Add the product of Part B (3.5 g) to a stirred solution of 4 M HCL in dioxane (25 ml) at 0° and stir for 0.5 hours. Evaporate the solvent and triturate the residue with ether to obtain 1-(S)-methoxycarbonyl-5-amino-pentyn-3-yl-(S)-alanine, t-butyl ester, hydrochloride.

D. Add N-methylmorpholine (1.5 g) to a solution of the product of Part C (2.9 g) in tetrahydrofuran at 0°. Add 6-chloro-3,4-dihydro-2-(phenylethyl)-2H-1,2,4-benzothiadiazine-7-sulfonyl chloride, S, S-dioxide (3.9 g) (See Preparation 2) and stir the resulting mixture at room temperature overnight. Dilute the reaction mixture with ethyl acetate, wash with 0.5 N HCl (1×), saturated sodium bicarbonate (2×), and brine (1×), dry over MgSO4 and evaporate the solvent. Chromatograph on silica gel, eluting with ethyl acetate:dichloromethane to obtain a residue.

E. Add the product of Part D (4.8 g) to a 4 M solution of HCL in dioxane (100 ml) and stir the resulting mixture at room temperature overnight. Evaporate the solvent then triturate the residue with ether to obtain a residue.

F. Treat the product of Part E in a manner similar to that described in Example 3, Part F, first paragraph, substituting (S)-proline, t-butyl ester for the octahydro-1H-indole, to obtain a residue.

Purify the resultant residue by chromatography on silica gel, eluting with ethyl acetate:CH2Cl2. Combine the desired fractions and evaporate the solvent to obtain a residue.

G. Treat the product of Part F in a manner similar to that described in Example 3, Part G to obtain the title compound.

EXAMPLE 9

N-[S-[[6-CHLORO-3,4,-DIHYDRO-3-(2-PHENYLETHYL)-2H-1,2,4-BENZOTHIADIAZIN-7-YL]SULFONYLAMINO]-1-(S)-METHOXYCARBONYL)-(E)-PENTEN-3-YL]-(S)-ALANYL-(S)-PROLINE, S,S-DIOXIDE,HYDROCHLORIDE

A. Add a solution of 1-N-acetylamino-1-(S)-carboxy-5-(t-butoxycarbonylamino)-3-pentyne (5 g) in tetrahydrofuran (20 ml) dropwise to a stirred solution of sodium (1.2 g) in liquid ammonia (1.2 L). After 2 h, add ammonium hydroxide and water. Remove the ammonia, dissolve the residue in ethyl acetate, wash with 0.5 N HCl (2×) and brine (3×), dry over MgSO4 and evaporate the solvent. Purify by precipitation from dichloromethane as the DCHA salt of (E)-1-N-acetylamino-1-carboxy-5-(t-butoxy-carbonylamino)-3-pentene.

B. Add cobalt chloride hexahydrate (50 mg) and Acylase I (aminoacylase from porcine kidney, grade 1, available from Sigma Chemical Co., St. Louis, Mo.) (100 mg) to a stirred solution of the product of Part A (3.5 g) in 0.1 M, pH 7.5 phosphate buffer (120 ml) at 38°. After 16 hours, remove the protein with activated carbon and filter through celite. Adjust pH of the solution to 2.75 and remove the unreacted isomer by washing with ethyl acetate (3×). Adjust the pH to 6.5 and evaporate the solvent. Remove the salt from the residue by dissolving in ethanol (100 ml) and filtering through celite. Evaporate the solvent to obtain (E)-1-amino-1-(S)-carboxy-5-(t-butoxycarbonylamino)-3-pentene.

C. Substitute the product of Part B (i.e., the 3-pentene compound) for the 3-pentyne compound in the procedure of Example 8, Parts B to G to obtain the title compound.

EXAMPLE 10

1-[2-(S)-[[2-[4-[[[6-CHLORO-3-CHLOROMETHYL--3,4-DIHYDRO-2H-1,2,4-BENZOTHIADIAZIN-7-YL]SULFONYLAMINO]METHYL]PHENYL-1-(S)-(ETHOXYCARBONYL)PROPYL]AMINO]-1-OXOPROPYL]-(2S-(2α,3aα,7aα)]-OCTAHYDRO-1-H-INDOLE-2-CARBOXYLIC ACID, T-BUTYL ESTER, S,S-DIOXIDE

A. To 1 g of the compound of Example 3, part B, in THF, add HCl-saturated dioxane (30 ml). Stir the mixture at room temperature for 5 hours under an inert atmosphere. Evaporate the solvent to obtain a dry foam as a hydrochloride salt.

B. Combine 3 g of the product of Part A with 2.5 g of octahydroindole-t-butyl ester (Preparation 3) in the manner described in Example 3, Part F to obtain 1-[2(S)-[[p-cyanophenyl-1(S)-(ethoxycarbonyl)propyl-]amino]-1-oxopropyl]-[2S-(2α,3aα,7aα)]-octahydro-1H-indole-2-carboxylic acid, t-butyl ester. FAB mass spec. M/e=501 (M+).

C. Hydrogenate 2.5 g of the product of Part B in 150 ml of ethyl alcohol containing 5 ml of saturated HCl/dioxane at 55 psi in the presence of 500 mg of 10% Pd on C for 20 hours. Filter the resultant reaction mixture through celite to obtain 2.6 g of amine.

D. Combine 850 mg of the product of Part C with 600 mg of 6-chloro-3-chloromethyl-3,4-dihydro-2H-1,2,4-benzothiadiazin-7-sulfonyl chloride, S,S-dioxide in 5 ml of THF containing 0.8 ml of N-methylmorpholine and let stand overnight at room temperature. Dilute with EtOAC, wash with saturated NaCl, and evaporate the solvent. Purify the resultant residue by chromatography on SiO2 with CH2Cl2/EtOAC as eluant to produce 700 mg of title compound. FAB mass spectrum shows M/e=844 (M+).

EXAMPLE 11

N-[N-[4-[4-[[[[6-CHLORO-3,4-DIHYDRO-3-[2-(2-PYRIDINYL)ETHYL]-2H-1,2,4-BENZOTHIADIAZIN-7-YL]SULFONYLAMINO]METHYL]-PHENYL]-1-(S)-ETHOXYCARBONYL)PROPYL]-(S)-ALANYL-(S)-PROLINE, T-BUTYL ESTER, S,S-DIOXIDE

A. To 6 g of the amine of Example 3, Part C, in 25 ml of DME cooled with an ice-bath, add 1.9 ml of N-methylmorpholine. To this mixture add 5 g of 4-amino-3-chloro-5-sulfonamidobenzenesulfonyl chloride in 25 ml of DME. Stir the reaction overnight with cooling under an inert atmosphere. Concentrate the resultant reaction mixture and partition the residue between EtOAc and H2O. Separate the organic layer and evaporate the solvent. Purify the resultant residue by chromatography on SiO2 using EtOAc/Hexanes as eluant to obtain 5 g of an oil. FAB mass spectrum M/e=633 (M+).

B. Treat the product of Part A in a manner similar to that described in Example 10, Part A, to yield a dry foam. FAB mass spectrum M/e=614 (M+).

C. Combine 1.6 g of the product of Part B with 490 mg L-proline, t-butyl ester in the presence of 9 ml of DMF, 380 mg 1-hydroxybenzotriazole, 1.14 ml N-methylmorpholine and 550 mg DEC. Stir the reaction overnight, then extract and purify the resultant product as described in Example 3, Part F, using EtOAc/Hexanes as eluent to obtain a residue, FAB mass spectrum M/e=730 M+.

D. In 7 ml THF, combine the amino-sulphonamide obtained in Part C with 360 mg of (2-pyridinyl)propanal and 10 mg of p-toluenesulfonic acid and stir for 24 hours at room temperature in an inert atmosphere. Concentrate the reaction mixture and partition the resultant residue between EtOAc and water. Separate the organic phase, wash with dilute NaHSO3, saturated NaHHCO3, saturated NaCl and dry with MgSO4. Evaporate the solvent and chromatograph the residue on SiO2 using EtOAc as eluant to obtain 350 mg of the title compound. Mass spectrum, M/e=899 (M+).

EXAMPLE 12

1-[N-[2-[4-[[[6-CHLORO-3,4-DIHYDRO-3-(2-PHENYLETHYL)-2H-1,2,4-BENZOTHIADIAZIN-7-YL]SULFONYL]AMINOMETHYL]-THIAZOL-2-YLMETHYLTHIO]-1(S)-(METHOXYCARBONYL)ETHYL]-(S)-ALANYL]-CIS,SYN-OCTAHYDROINDOLE-2(S)-CARBOXYLIC ACID, S,S-DIOXIDE (A) Ethyl-4-Aminomethylthiazole-2-Carboxylate

1. Ethyl-thizaole-4-Carboxylate

Combine ethylbromopyruvate (19.5 g, 100 mmole) in 50 ml EtOH and thioformamide (4.27 g, 70 mmole) in 10 ml EtOH and stir at room temperature overnight. Pour into 1 N HCl (100 ml) and extract with 190 ml diethyl ether. Separate the aqueous layer and treat with an excess of solid sodium bicarbonate. Extract the aqueous layer with diethylether (2×150 ml), dry over $MgSO_4$ and evaporate the solvent to obtain the title compound of Part A(1) as a syrup. Recrystallize from hexanes to obtain white needles, m.p. 52°–54° C.

2. 2-Carboamide-Thiazole

Treat 5.0 g of the product of Part A(1) with 100 ml of concentrated ammonium hydroxide solution overnight. Purge with $N_2$ for 2 hours and remove the solvent to obtain a crude product. Recrystallize using ethylacetate/pet ether to obtain the title compound, m.p. 122°–124° C.

3. 4-Cyano-Thiazole

Dissolve the product of Part A(2) (2.0 g, 14.50 mmoles) in 20 ml of dry $CH_2Cl_2$ and cool in an ice bath. Add trifluoroacetic anhydride (3.65 g, 16.50 mmoles) and stir at room temperature for 3 hours. Evaporate the solvent and recrystallize from ethylacetate/pet ether to obtain the title compound, m.p. 54°–56° C.

4. Ethyl-4-Cyanothiazole-2-Carboxylate

Cool diisopropyl amine (4.04 g, 40.0 mmoles) in dry THF in an ice bath under nitrogen. Add n-butyl lithium (40 ml, 40 mmoles) and stir at 0° C. for 15 min. Cool the resultant reaction mixture to −78° C. and add a solution of the product of part A(3) (4.0 g, 36.36 mmoles) in 20 ml THF. Stir the reaction mixture at −78° C. for 30 minutes, add ethylchloroformate (3.93 g, 36.36 mmoles) and slowly warm the reaction mixture to room temperature. Add aqueous ammonium chloride and evaporate the solvent. Add $CH_2Cl_2$ (300 ml) to the resultant residue, wash with water, dry over $MgSO_4$ and evaporate the solvent to obtain the title compound. Purify the product by column chromatography using ethylacetate/pet ether.

5. Ethyl-4-Aminomethylthiazole-2-Carboxylate

Cool a disiamylborane (17.50 mmoles) solution in an ice bath under nitrogen. Add the product of Part A(4) (1.5 g, 8.24 mmoles) in 10 ml of dry THF and let stand at 0° C. for 2 days. Pour the reaction mixture into ice cold 1N HCl and extract with diethyl ether. Separate the aqueous layer, treat with sodium bicarbonate, extract with 2×100 ml ethyl acetate, dry over $MgSO_4$ and evaporate the solvent to obtain the title compound. Use without further purification in Part B.

B.
1-N-[2-[4-[6-Chloro-3,4-Dihydro-3-(2-Phenylethyl)-2H-1,2,4,-Benzothiadiazin-7-yl]Sulfonyl]Aminomethyl]-2-Carboethoxythiazole, S,S-Dioxide Combine the product of Preparation 2 (1.2 mmoles) and the product of Part A (1.0 mmoles) in dry DMF (1.0 ml) and cool in an ice bath. Add dropwise triethyl amine (1.5 mmoles). Stir the resulting reaction mixture at room temperature for 16 hours. Evaporate the solvent under high vacuum, take up the residue in ethylacetate (100 ml), wash with water, dry over $MgSO_4$ and evaporate the solvent. Purify the resultant residue by column chromatography.

C.
1-[N-[2-[4-[6-Chloro-3,4-Dihydro-3-(2-Phenylethyl)-2H-1,2,4-Benzothiadiazin-7-yl]Sulfonyl]Aminomethyl]-2-Hydroxymethylthiazole, S,S-Dioxide Dissolve the product of Part B (1.0 mmole) in 25 ml dry THF and cool to −40° C. under nitrogen. Add $LiALH_4$ (1.5 mmole) and stir the resultant mixture at −40° C. for 1 hour. Add $Na_2SO_4:10H_2O$, filter, dry over $MgSO_4$ and evaporate the solvent to obtain the title compound.

D.
1-[N-[2-[4-[6-Chloro-3,4-Dihydro-3-(2-Phenylethyl)-2H-1,2,4-Benzothiadiazin-7-yl]Sulfonyl]Aminomethyl]-2-Bromomethylthiazole, S,S-Dioxide Combine carbon tetrabromide (1.1 mmoles) and triphenyl phosphine (1.1 mmoles) in dry DMF (5 ml) at 0° C. under nitrogen and stir at 0° C. for ½ hour. Add a solution of the product of Part C (1.0 mmoles) in dry DMF (3 ml) and stir the reaction mixture at 0° C. for 1–2 hours. (Check progress of reaction by TLC). Pour the resultant mixture into ice cold water, extract with diethyl ether (2×150 ml), dry over $MgSO_4$ and evaporate the solvent. Purify the resultant residue by column chromatography.

E.
Bis[[[1-(S)-(Methoxycarbonyl)-Ethyl]-(S)-Alanyl]-Cis,-Syn-Octahydroindole-2(S)-tert-Butoxycarbonyl]-disulphide 1. Cool a solution of L-cysteine (7.20 g, 0.027 moles) in 50 ml dry $CH_2Cl_2$ in an ice bath under $N_2$. Add N-methylmorpholine (16.8 g, 0.16 moles), then add a freshly prepared solution of triflate reagent (0.161 moles) (Preparation 1) in 200 ml $CH_2Cl_2$ dropwise over 2 hours. Stir the resulting reaction mixture overnight at room temperature. Wash the reaction mixture with 2×100 ml of water, then 2×100 ml of Column chromatograph the resultant residue using 40% ethyl acetate:60% pet ether to obtain a syrup.

2. Cool a solution of the product of Part E(1) in 50 ml dioxane in an ice bath. Add 150 ml of a solution of saturated dioxane:HCl and stir at room temperature for 3 hours. Reduce the volume of the reaction mixture to 50 ml and add 150 ml of ethyl acetate to precipitate the product as the hydrochloride salt.

3. Cool a solution of the product of Part E(2) (1.0 mmole) in 10 ml dry DMF in an ice bath. Add 1-hydroxybenzotriazole hydrate (2.2 mmoles), 1-(dimethylaminopropyl)-3-ethyl-carbodiimide (3.0 mmole) and 2-carboxy-perhydroindole t-butyl ester (2.3 mmole) (Preparation 3) and stir the resulting solution at 0° C. Add triethylamine dropwise (6.0 mmoles) and stir the resulting reaction mixture over-night at room temperature. Evaporate the solvent, dissolve the residue in 200 ml of ethylacetate, wash with water, brine, and dry over MgSO$_4$. Evaporate the solvent and column chromatograph the resultant residue using 60% ethylacetate:40% pet ether.

F. Cool 5 ml of dry methanol in an ice bath under nitrogen, add sodium borohydride (10.0 mmole) and stir at 0° C. for 10 minutes. Add the product of Part E (0.60 mmoles) in 5 ml dry methanol and stir the resulting mixture for 5 minutes at 0° C. Add the product of Part D (1.2 mmoles) in 5 ml THF, warm the mixture to room temperature and stir at room temperature for 2 hours. Evaporate the solvent and take up the resultant residue in ethylacetate. Extract with 10% citric acid, NaHHCO$_3$ solution and brine, dry over MgSO$_4$ and evaporate the solvent. Chromatograph the residue to obtain the t-butyl ester of the title compound of Example 12.

G. Treat the product of Part F in a manner similar to that described in Example 3, Part G, to obtain the title compound. Mass spectrum m/e=925 (M+).

EXAMPLE 13

1-[2(S)-[[4-[4-[[[6-CHLORO-3,4-DIHYDRO-3-(1-IMIDAZOLYLMETHYL)-2H-1,2,4-BENZO-THIADIAZIN-7-YL]SULFONYLAMINO]METHYL]PHENYL]-1(S)-(ETHOXYCARBONYL)-BUTYL]AMINO]-1-OXOPROPYL]-CIS,SYN-OCTAHYDROINDOLE-2(S)-CARBOXYLIC ACID, DIHYDROCHLORIDE

A. Substituting 2-(4-cyano)phenylpropyl bromide for 2-(4-cyano)phenylethyl bromide, carry out the procedure described in Example 3, Parts A–C to obtain the hydrochloride salt.

B. Treat the product of Part A as described in Example 11, Parts A and B, to obtain a residue.

C. Combine the product of Part B and perhydroindole-2-carboxylic acid, t-butyl ester (Preparation 3) as described in Example 11, part C and stir overnight. Evaporate the solvent and partition the resultant residue between 5% NaHHCO$_3$ and EtOAc. Separate the EtOAc layer, dry over MgSO$_4$ and evaporate the solvent. Chromatograph the resultant residue by flash chromatography on SiO$_2$ (150 gm) eluting with 60% EtOAc: 40% hexane. Combine the desired fractions and evaporate the solvent to obtain a residue.

D. Dissolve sodium spheres (2.3 g) in dry methanol (100 ml) at room temperature, add imidazole (6.3 ml) and stir for 1 hour at room temperature. Add bromoacetaldehyde dimethylacetal (11.8 ml) and heat the resultant mixture overnight at reflux. Evaporate the solvent in vacuo, partition the resultant residue between EtOAc and water, dry the organic layer over MgSO$_4$, and evaporate the solvent. Purify the resultant residue by flash chromatography on SiO$_2$ (250 g), eluting with 4% CH$_3$OH in CH$_2$Cl$_2$. Combine the desired fractions and evaporate the solvent to obtain (1-imidazolyl)acetaldehyde dimethylacetal.

E. Combine the products of Part C (0.50 g) and Part D (0.13 g) in THF (20 ml), add HCl-saturated dioxane and stir, following the reaction by thin layer chromatography on silica gel (elute with 5% CH$_3$OH in CH$_2$Cl$_2$) and adding HCl-dioxane until the reaction is complete. Evaporate the solvent, partition the resultant residue between 5% NaHHCO$_3$ and EtOAc, wash the organic layer with brine, dry over MgSO$_4$, and evaporate the solvent to obtain a residue. Purify the resultant residue by flash chromatography on SiO$_2$ (25 g), eluting with 3% CH$_3$OH in CH$_2$Cl$_2$. Combine the desired fractions and evaporate the solvent to obtain the t-butyl ester of the title compound.

F. Stir the product of Part E in HCl-saturated dioxane (200 ml) at room temperature and under nitrogen for 6 hours. Evaporate the solvent in vacuo at room temperature to obtain the title compound, M/e=834 (M+).

In a similar manner, using appropriate starting materials and reagents, the following compounds may be prepared:

1-[2-(S)-[[1-(S)-carboxy-2-[4-[[[6-chloro-3-(cyclopentylmethyl)-3,4-dihydro-2H-1,2,4-benzothiadiazin-7-yl]sulfonylamino]methyl]phenylmethoxy]ethyl]amino]-1oxopropyl]-[2S-(2α, 3aα, 7aα)]-octahydro-1H-indole-2-carboxylic acid, S,S-dioxide 1-[2-[[1-(S)-carboxy-2-[4-[[[6-chloro-3-(dichloromethyl)-3,4-dihydro-2H-1,2,4-benzothiadiazin-7-yl]sulfonylamino]methyl]phenylmethoxy]ethyl]amino]-1oxopropyl]-[2S-(2α, 3aα, 7aα)]-octahydro-1H-indole-2-carboxylic acid, S,S-dioxide 1-[2-(S)-[[1-(S)-carboxy-3-[4-[[[6-chloro-3,4-dihydro-3-(2-phenylethyl)-2H-1,2,4-benzothiadiazin-7-yl]sulfonylamino]methyl]phenyl]propyl]amino]-1oxopropyl]-[2S-(2α, 3aα, 7aα)]-octahydro-1H-indole-2-carboxylic acid, S,S-dioxide 1-[2-(S)-[[1-(S)-carboxy-3-[4-[[[6-chloro-3-(cyclopentylmethyl)-3,4-dihydro-2H-1,2,4-benzothiadiazin-7-yl]sulfonylamino]methyl]phenyl]propyl]amino]-1-oxopropyl]-[2S-(2α, 3aα, 7aα)]-octahydro-1H-indole-2-carboxylic acid, S,S-dioxide 1-[2-(S)-[[1-(S)-carboxy-3-[4-[[[6-chloro-3-(dichloromethyl)-3,4-dihydro-2H-1,2,4-benzothiadiazin-7-yl]sulfonylamino]methyl]phenyl]propyl]amino]-1oxopropyl]-[2S-(2α, 3aα, 7aα)]-octahydro-1H-indole-2-carboxylic acid, S,S-dioxide 1-[2-(S)-[[1-(S)-carboxy-2-[4-[[[6-chloro-3,4-dihydro-3-(2-phenylethyl)-2H-1,2,4-benzothiadiazin-7-yl]sulfonylamino]methyl]phenyl]ethyl]amino]-1-oxopropyl]-[2S-(2α, 3aα, 7aα)]-octahydro-1H-indole-2-carboxylic acid, S,S-dioxide N-[1-(S)-carboxy-3-[4-[[[6-chloro-3,4-dihydro-3-(2-phenylethyl)-2H-1,2,4-benzothiadiazin-7-yl]sulfonylamino]methyl]phenyl]propyl]-(S)-alanyl-(S)-proline, S,S-dioxide N-[1-(S)-carboxy-3-[4-[[[6-chloro-3-(cyclopentylmethyl)-3,4-dihydro-2H-1,2,4-benzothiadiazin-7-yl]sulfonylamino]methyl]phenyl]propyl]-(S)-alanyl-(S)proline, S,S-dioxide N-[1-(S)-carboxy-3-[4-[[[6-chloro-3-(dichloromethyl)-3,4-dihydro-2H-1,2,4-benzothiadiazin-7-yl]sulfonylamino]methyl]phenyl]propyl]-(S)-alanyl-(S)-proline, S,S-dioxide N-[1-(S)-carboxy-2-[4-[[[6-chloro-3,4-dihydro-3-(2-phenylethyl)-2H-1,2,4-benzothiadiazin-7-yl]sulfonylamino] methyl]phenyl]ethyl]-(S)-alanyl-(S)-proline, S,S-dioxide N-[1-(S)-carboxy-3-[4-[[[6-chloro-3,4-dihydro-3-(2-phenylethyl)-2H-1,2,4-benzothiadiazin-7-yl]sulfonylamino]methyl]phenyl]propyl]-(S)-alanyl-(S)-(4-cyclohexyl)proline, S,S-dioxide 7-N-[2-(S)-[[1-(S)-carboxy-3-[4-[[[6-chloro-3,4-dihydro-3-(2-phenylethyl)-2H-1,2,4-benzothiadiazin-7-yl]sulfonylamino]methyl]phenyl]propyl]amino]-1-oxopropyl]-1,4-dithia-7-azaspiro[4.4]nonane-8-(S)-carboxylic acid, S,S-dioxide 1-[2-(S)-[[1-(S)-carboxy-3-[4-[[[6-chloro-3,4-dihydro-3-(2-phenylethyl)-2H-1,2,4-benzothiadiazin-7-yl]sulfonylamino]methyl]phenyl]propyl]amino]-1-oxopropyl]-1H-2,3-dihydroindole-2-(S)-carboxylic acid S,S-dioxide 1-[2-(S)-[[2-[4-[[[6-chloro-3,4-dihydro-3-(2-phenylethyl)-2H-1,2,4-benzothiadiazin-7-yl]sulfonylamino]methyl]phenylmethoxy]-1-(S)-[(2,2-dimethyl-1,3-dioxolan-4-yl)methoxycarboxyl]ethyl]amino]-1-oxopropyl]-[2S-(2α, 3aα, 7aα)]-octahydro-1H-indole-2-carboxylic acid, S,S-dioxide 1-[2-(S)-[[3-[4-[[[6-chloro-3,4-dihydro-3-(2-phenylethyl)-2H-1,2,4-benzothiadiazin-7-yl]sulfonylamino]methyl]phenyl]-1-(S)-[(2,2-dimethyl-1,3-dioxolan-4-yl)methoxycarbonyl]propyl]amino]-1-oxopropyl]-[2S-(2α, 3aα, 7aα)]-octahydro-1H-indole-2-carboxylic acid, S,S-dioxide 1-[2-(S)-[[3-[4-[[[6-chloro-3,4-dihydro-3-(2-phenylethyl)-2H-1,2,4-benzothiadiazin-7-yl]sulfonylamino]methyl]phenyl]-1-(S)-(ethoxycarbonyl)propyl]amino]-1-oxopropyl]-[2S-(2α, 3aα, 7aα)]-octahydro-1H-indole-2-carboxylic acid, S,S-dioxide N-[3-[4-[[[6-chloro-3,4-dihydro-3-(2-phenylethyl)-2H-1,2,4-benzothiadiazin-7-yl]sulfonylamino]methyl]phenyl]-1-(S)(ethoxycarbonyl)propyl]-(S)-alanyl-(S)-proline, S,S-dioxide N-[3-[4-[[[6-chloro-3,4-dihydro-3-(2-phenylethyl)-2H-1,2,4-benzothiadiazin-7-yl]sulfonylamino]methyl]phenyl]-1-(S)-[(2-phenoxy)ethoxycarbonyl]propyl]-(S)-alanyl-(S)-proline, S,S-dioxide.

N-[3-[4-[[[6-chloro-3,4-dihydro-3-(2-phenylethyl)-2H-1,2,4-benzothiadiazin-7-yl]sulfonylamino]methyl]phenyl]-1-(S)-[(2,3-dihydroxy)propoxycarbonyl]propyl]-(S)-alanyl-(S)-proline, S,S-dioxide.

N-[3-[4-[[[6-chloro-3-(cyclopentylmethyl)-3,4-dihydro-2H-1,2,4-benzothiadiazin-7-yl]sulfonylamino]methyl]phenyl]-1-(S)-(ethoxycarbonyl)propyl]-(S)-alanyl-(S)-proline, S,S-dioxide N-[3-[4-[[[6-chloro-3,4-dihydro-3-(2-phenylethyl)-2H-1,2,4-benzothiadiazin-7-yl]sulfonylamino]methyl]phenyl]-1-(S)-[(2,2-dimethyl-1,3-dioxolan-4-yl)methoxycarbonyl]propyl]-(S)-alanyl-(S)-proline, S,S-dioxide N-[3-[4-[[[6-chloro-3-(cyclopentylmethyl)-3,4-dihydro-2H-1,2,4-benzothiadiazin-7-yl]sulfonylamino]methyl]phenyl]-1-(S)-[(2,2-dimethyl-1,3-dioxolan-4yl)methoxycarbonyl]propyl]-(S)-alanyl-(S)-proline, S,S-dioxide N-[3-[4-[[[6-chloro-3-(cyclopentylmethyl)-3,4-dihydro-2H-1,2,4-benzothiadiazin-7-yl]sulfonylamino]methyl]phenyl]-1-(S)-[(2-phenoxy)ethoxycarbonyl]propyl]-(S)-alanyl-(S)-proline, S,S-dioxide N-[3-[4-[[[6-chloro-3-(cyclopentylmethyl)-3,4-dihydro-2H-1,2,4-benzothiadiazin-7-yl]sulfonylamino]methyl]phenyl]-1-(S)-[(2,3-dihydroxy)propoxycarbonyl]-propyl]-(S)-alanyl-(S)-proline, S,S-dioxide 1-[2-[[2-[[4-[[[4-chloro-3-[[(phenylmethyl)amino]sulfonyl]phenyl]sulfonylamino]methyl]phenyl]methoxy]-1-(S)-(ethoxycarbonyl)ethyl]amino]-1-oxopropyl]-[2S(2α, 3aα,7aα)]-octahydro-1H-indole-2-carboxylic acid 1-[2-[[2-[[4-[[[4-chloro-3-[[(phenylmethyl)amino]-sulfonyl]phenyl]sulfonylamino]methyl]phenyl]methoxy]-1-(S)-(carboxy)ethyl]amino]-1-oxopropyl]-[2S-(2α,3aα,7aα)]-octahydro-1H-indole-2-carboxylic acid N-[2-[[4-[[[4-chloro-3-[[(phenylmethyl)amino]sulfonyl]phenyl]sulfonylamino]methyl]phenyl]methoxy]-1-(S)-(ethoxycarbonyl)ethyl]-(S)-alanyl-(S)-proline N-[2-[[4-[[[4-chloro-3-[[(phenylmethyl)amino]-sulfonyl]phenyl]sulfonylamino]methyl]phenyl]methoxy]-1-(S)-(carboxy)ethyl]-(S)-alanyl-(S)-proline 1-[2-[[2-[[4-[[[3-(amino)sulfonyl-4-chlorophenyl]-sulfonylamino]methyl]phenyl]methoxy]-1-(S)(ethoxycarbonyl)ethyl]amino]-1-oxopropyl]-[2S(2α,3aα,7aα)]-octahydro-1H-indole-2-carboxylic acid 1-[2-[[2-[[4-[[[3-(amino)sulfonyl-4-chlorophenyl]-sulfonylamino]methyl]phenyl]methoxy]-1-(S)-(carboxy)ethyl]amino]-1-oxopropyl]-[2S-(2α,3aα,7aα)]-octahydro-1H-indole-2-carboxylic acid N-[2-[[4-[[[3-(amino)sulfonyl-4-chlorophenyl]-sulfonylamino]methyl]phenyl]methoxy]-1-(S)(ethoxycarbonyl)ethyl]-(S)-alanyl-(S)-proline N-[2-[[4-[[[3-(amino)sulfonyl-4-chlorophenyl]sulfonylamino]methyl]phenyl]methoxy]-1-(S)(ethoxycarbonyl)ethyl]-(S)-lysyl-(S)-proline N-[2-[[4-[[[3-(amino)sulfonyl-4-chlorophenyl]sulfonylamino]methyl]phenyl]methoxy]-1-(S)(carboxy)ethyl]-(S)-alanyl-(S)-proline N-[2-[[4-[[[3-(amino)sulfonyl-4-chlorophenyl]sulfonylamino]methyl]phenyl]methoxy]-1-(S)-(carboxy)-ethyl]-(S)-lysyl-(S)-proline N-[2-[[4-[[[3-(amino)sulfonyl-4-chlorophenyl]-sulfonylamino]methyl]phenyl]methoxy]-1-(S)-[(2,2-dimethyl-1-oxopropoxy)methoxycarbonyl]ethyl]-(S)-alanyl-(S)-proline N-[3-[4-[[[6-chloro-3,4-dihydro-2H-1,2,4-benzothiadiazin-7-yl]sulfonylamino]methyl]phenyl]-1-(S)(ethoxycarbonyl)propyl]-(S)-alanyl-(S)-proline, S, S-dioxide N-[3-[4-[[[6-chloro-3,4-dihydro-2H-1,2,4-benzothiadiazin-7-yl]sulfonylamino]methyl]phenyl]-1-(S)-[2,2-dimethyl-1-oxopropoxy)methoxycarbonyl]propyl]-(S)-alanyl-(S)-proline, S, S-dioxide N-[3-[4-[[[6-chloro-3,4-dihydro-2H-1,2,4-benzothiadiazin-7-yl]sulfonylamino]methyl]phenyl]-1-(S)(ethoxycarbonyl)propyl]-(S)-lysyl-(S)-proline, S, S-dioxide N-[1-(S)-carboxy-3-[4-[[[6-chloro-3,4-dihydro-2H-1,2,4-benzothiadiazin-7-yl]sulfonylamino]methyl]phenyl]propyl]-(S)-alanyl-(S)-proline, S, S-dioxide N-[1-(S)-carboxy-3-[4-[[[6-chloro-3,4-dihydro-2H-1,2,4-benzothiadiazin-7-yl]sulfonylamino]methyl]phenyl]propyl]-(S)-lysyl-(S)-proline, S, S-dioxide N-[1-(S)-carboxy-3-[4-[[[6-chloro-3-chloromethyl-3,4-dihydro-2H-1,2,4-benzothiadiazin-7-yl]-sulfonylamino]methyl]phenyl]propyl]-(S)-alanyl-(S)-proline, S, S-dioxide N-[1-(S)-carboxy-3-[4-[[[6-chloro-3-chloromethyl-3,4-dihydro-2H-1,2,4-benzothiadiazin-7-yl]sulfonylamino]methyl]phenyl]propyl]-(S)-lysyl-(S)-proline, S, S-dioxide N-[3-[4-[[[6-chloro-3-chloromethyl-3,4-dihydro-2H-1,2,4-benzothiadiazin-7-yl]sulfonylamino]methyl]phenyl]-1-(S)-[2,2-dimethyl-1-oxopropoxy)methoxycarbonyl]propyl]-(S)-alanyl-(S)-proline, S, S-dioxide N-[3-[4-[[[6-chloro-3-chloromethyl-3,4-dihydro-2H-1,2,4-benzothiadiazin-7-yl]sulfonylamino]methyl]phenyl]-1-(S)-(ethoxycarbonyl)propyl]-(S)-alanyl-(S)-proline, S, S-dioxide 1-[2-(S)-[[2-[4-[[[6-chloro-3-chloromethyl-3,4-dihydro-2H-1,2,4-benzothiadiazin-7-yl]sulfonylamino]methyl]phenylmethoxy]-1-(S)-(ethoxycarbonyl)ethyl- ]amino]-oxopropyl]-[2S-(2α,3aα,7aα)]-octahydro-1H-indole-2-carboxylic acid, S, S-dioxide 1-[2-(S)-[[1-(S)-carboxy-2-[4-[[[6-chloro-3-chloromethyl-3,4-dihydro-2H-1,2,4-benzothiadiazin-7-yl]sulfonylamino]methyl]phenyl]ethyl]amino]-1-oxopropyl]-2S-(2α,3aα,7aα)]-octahydro-1H-indole-2-carboxylic acid, S, S-dioxide 1-[2-(S)-[[1-(S)-carboxy-2-[4-[[[6-chloro-3-chloromethyl-3,4-dihydro-2H-1,2,4-benzothiadiazin-7-yl]sulfonylamino]methyl]phenylmethoxy]ethyl]amino]-1oxopropyl]-[2S-(2α,3aα,7aα)]-octahydro-1H-indole-2-carboxylic acid, S, S-dioxide 1-[2-(S)-[[1-(S)-carboxy-2-[4-[[[6-chloro-3,4-dihydro-2H-1,2,4-benzothiadiazin-7-yl]sulfonylamino]methyl]phenylmethoxy]ethyl]amino]-1-oxopropyl]-[2S-(2α,3aα,7aα)]-octahydro-1H-indole-2-carboxylic acid, S, S-dioxide N-[1-(S)-carboxy-5-[6-chloro-3,4-dihydro-2H-1,2,4-benzothiadiazin-7-yl]sulfonylamino]pentyn-3-yl]-(S)-alanyl-(S)-proline, S, S-dioxide N-[5-[6-chloro-3,4-dihydro-2H-1,2,4-benzothiadiazin-7-yl]-sulfonylamino]-1-(S)-(ethoxycarbonyl)pentyn-3-yl]-(S)-alanyl-(S)-proline, S, S-dioxide 1-[4-carboxy-5-[4-[[[6-chloro-3-(cyclopentylmethyl)-3,4-dihydro-2H-1,2,4-benzothiadiazin-7-yl]sulfonylamino]methyl]phenylmethoxy]-1-oxopentyl]-octahydro-1H-indole-2-carboxylic acid, S, S-dioxide N-[2-(S)-[1-(S)-carboxy-3-[4-[[[6-chloro-3,4-dihydro-3-(2-phenylethyl)-2H-1,2,4-benzothiadiazin-7-yl]sulfonyl-amino]methyl]phenyl]propoxy]-1-oxopropyl]-(S)-proline, S, S-dioxide N-[N-[3-[5-[[[[6-chloro-3,4-dihydro-3-(2-phenylethyl)-2H-1,2,4-benzothiadiazin-7-yl]sulfonyl]amino]methyl]-1H-imidazol-2-yl]-1-(ethoxycarbonyl)propyl]-(S)-alanyl-(S)-proline, S,S-dioxide N-[N-[3-[5-[[[[6-chloro-3,4-dihydro-3-(2-phenylethyl)-2H-1,2,4-benzothiadiazin-7-yl]sulfonyl]amino]methyl]-2-thiazolyl]-1-(ethoxycarbonyl)propyl]-(S)-alanyl-(S)-proline, S,S-dioxide The following are non-limiting examples of a topical ophthalmic formulations of the invention. Compound A refers to 1-[2-(S)-[[1-(S)-carboxy-5-[[6-chloro-3-chloromethyl-3,4-dihydro-2H-1,2,4-benzothiadiazin-7-yl]sulfonylamino]pentyl]amino]-1-oxopropyl]-[2S-(2α, 3aα, 7aα)]-octahydro-1H-indole-2-carboxylic acid, S,S-dioxide. It is contemplated, however, that therapeutically effective amounts of other compounds of formula I may be substituted in its place.

EXAMPLE A

| Topical Solution: Ingredients | mg/ml |
|---|---|
| Compound A | 0.01 |
| Dibasic Sodium Phosphate | 10.4 |
| Monobasic Sodium Phosphate | 2.4 |
| Chlorobutanol | 5.0 |
| Hydroxypropyl methylceluose | 5.0 |
| Sterile Water | q.s. ad 1.0 ml |
| 1.0N NaOH | q.s. ad pH 7.4 |

Mix the ingredients under sterile conditions and using standard techniques to obtain the ophthalmological solution.

| Topical Solution: Ingredients | mg/ml |
|---|---|
| Compound A | 0.01 |
| Timolol | 5.0 |
| Dibasic Sodium Phosphate | 10.4 |
| Monobasic Sodium Phosphate | 2.4 |
| Chlorobutanol | 5.0 |
| Hydroxypropyl methylceluose | 5.0 |
| Sodium Hydroxide or Hydrochloric Acid | q.s. ad pH 7.4 |
| Sterile Wter | q.s. ad 1.0 ml |

Mix the ingredients under sterile conditions and using standard techniques to obtain the ophthalmological solution.

Other beta adrenergic blocking agents may be used in the above examples, such as bulonol.

EXAMPLE C

| Topical Solution: Ingredients | mg/ml |
|---|---|
| Compound A | 0.01 |
| Dexamethasone Sodium Phosphate | 1.0 |
| Dibasic Sodium Phosphate | 10.4 |
| Monobasic Sodium Phosphate | 2.4 |
| Chlorobutanol | 5.0 |
| Hydroxypropyl methylceluose | 5.0 |
| Sodium Hydroxide or Hydrochloric Acid | q.s. ad pH 7.4 |
| Sterile Wter | q.s. ad 1.0 ml |

Mix the ingredients under sterile conditions and using standard techniques to obtain the ophthalmological solution.

We claim:

1. A method for reducing intraocular pressure which comprises topically administering from about 0.000001% (w/v) to about 1.0% of an ophthalmologically acceptable composition to the eye of a mammal in need of such treatment comprising a compound of the formula I:

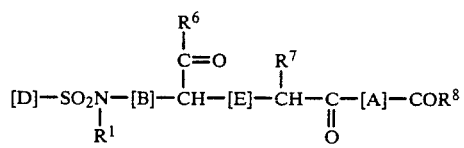

or a pharmaceutically acceptable salt thereof, wherein:
A is

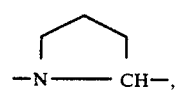
IIa

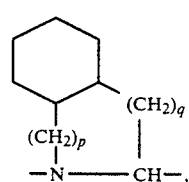
IIb

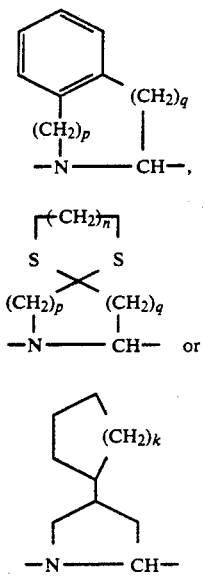

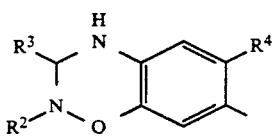

k is 1 or 2;
n is 0 or 1;
p and q are 0, 1 or 2, provided that in structures IIb and IIc the sum of p and q is 1 or 2, and that in formula IId, p is not 0;
B is —[J]—[L]—[M]—;
D is

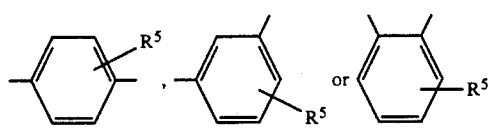

E is —NH—, —O—, —S—, or —CH$_2$—;
G is —SO$_2$—;
J is —(CH$_2$)$_s$— or —((CH$_2$)$_t$—W)—;
L is a chemical bond, cis- or trans-lower alkenylene, lower alkynylene, -Z-aryl-, -aryl-Z-, -Z-cycloalkyl-, or -cycloalkyl-Z-, a 5- or 6-membered heterocyclic radical comprising 3–5 carbon atoms and 1 or 2 heteroatoms selected from N, O and S, or a R$^5$-substituted heterocyclic radical, wherein aryl is

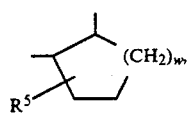

and cycloalkyl is

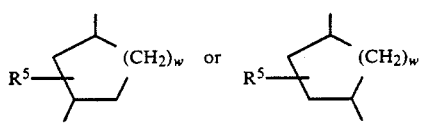

wherein w is 1, 2 or 3;
M is —(CH$_2$)$_u$— or —((CH$_2$)$_r$—X—(CH$_2$)$_v$)—;
W is

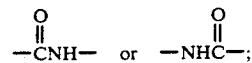

X and Z are independently a chemical bond, —NR$^9$—, —O—, —S—,

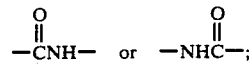

s, u and v are independently 0–5;
t is 1–5;
R$^1$, R$^2$ and R$^9$ are independently hydrogen, lower alkyl or lower acyl;
R$^3$ is hydrogen, lower alkyl, halo- and dihaloloweralkyl, trifluoroethylthiomethyl, phenylloweralkyl, (cycloalkyl)lower alkyl, aminomethyl, loweralkylaminomethyl, phenyl(lower)alkylthiomethyl, (cycloalkyl)loweralkylaminomethyl, 2-, 3- or 4-pyridyllower alkyl, 2-, 4- or 5-, thiazolyloweralkyl, 2-, 4- or 5-1H-imidazolylloweralyl, 1-imidazolylloweralkyl, 1-morpholinoloweralkyl or hydroxyphenylloweralkyl;
R$^4$ is chlorine or CF$_3$;
R$^5$ is hydrogen, halogen, lower alkyl, lower acyl, lower alkoxy, haloloweralkyl or phenylloweralkyl;
R$^7$ is hydrogen, lower alkyl or aminoloweralkyl;
R$^6$ and R$^8$ are independently hydroxy, alkoxy having from 1 to 8 carbon atoms, benzyl, allyl, R$^{10}$—O—$_r$—(CH$_2$)$_m$—O—, wherein O is oxygen or sulfur, r is 0 or 1 and
m is 2 to 4,

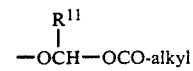

wherein the alkyl has from 3 to 8 carbon atoms,

wherein the phenyl may be substituted with group T defined below, 1-glyceryl,

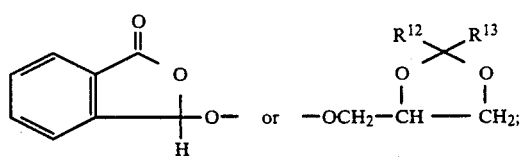

R$^{10}$ is phenyl, substituted phenyl wherein the substituents are chosen from group T, 1-naphthyl or 2-naphthyl;
T is halogen, hydroxy, trifluoromethyl, lower alkoxy, lower alkyl, 2-furanyl, 3-furanyl, 2-thienyl, 3-thienyl, phenyl and substituted phenyl wherein the substituents are chosen from halogen, hydroxy, trifluoromethyl, lower alkoxy or lower alkyl;
R$^{11}$ is hydrogen or alkyl having from 1 to 8 carbon atoms;

$R^{12}$ is hydrogen, lower alkyl, unsubstituted or substituted phenyl and substituted or unsubstituted phenyl lower alkyl, wherein phenyl may be substituted by group T; and $R^{13}$ is hydrogen or lower alkyl;

provided that if L is alkenylene or alkynylene, J is —$(CH_2)_s$— wherein s is 1–5; provided that if L is -Z-aryl-or -Z-cycloalkyl-, J is —$(CH_2)_s$— wherein s is 2–5; provided that if L is alkenylene, alkynylene; -aryl-Z- or -cycloalkyl-Z-, M is —$(CH_2)_u$— wherein u is 1–5; provided that if s and u are each zero, L is aryl or cycloalkyl (i.e. Z is a bond); and provided that if s and v are each zero, L is aryl or cycloalkyl (i.e. Z is a bond)

in combination with from about 0.01 to about 1.0% of a beta adrenergic blocking agent.

2. A method according to claim 1 wherein the beta adrenergic blocking agent and the compound of formula I are administered topically together in the same composition.

3. A method according to claim 2 wherein the beta adrenergic blocking agent is selected from atenolol, metoprolol, nadolol, pindolol, propranolol, timolol, labetalol, cartelol, bunolol, betaxolol or dilevalol or pharmaceutically acceptable salts and/or isomers thereof.

4. A method according to claim 2 wherein the beta adrenergic blocking agent is timolol.

5. A method according to claim 2 wherein the beta adrenergic blocking agent is bunolol.

6. A topical ophthalmologically acceptable composition useful for controlling elevated intraocular pressure which comprises from about 0.01 to about 1.0% of a beta adrenergic blocking agent, and from about 0.000001 to about 1.0% of a compound represented by the formula I:

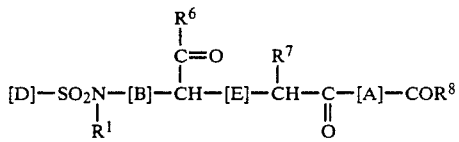

or a pharmaceutically acceptable salt thereof, in combination with an ophthalmologically acceptable carrier for topical use, wherein:

A is

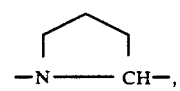  IIa

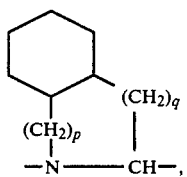  IIb

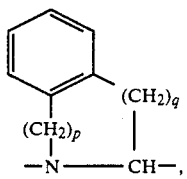  IIc

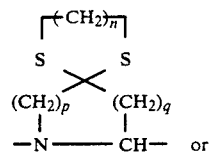  IId

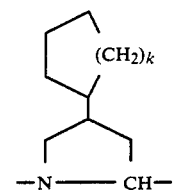  IIe k is 1 or 2;

n is 0 or 1;

p and q are 0, 1 or 2, provided that in structures IIb and IIc the sum of p and q is 1 or 2, and that in formula IId, p is not 0;

B is —[J]—[L]—[M]—;

D is

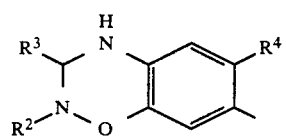  IIIa

E is —NH—, —O—, —S—, or —$CH_2$—;

G is —$SO_2$—

J is —$(CH_2)_s$— or —$((CH_2)_r$—W)—;

L is a chemical bond, cis- or trans-lower alkenylene, lower alkynylene, -Z-aryl-, -aryl-Z-, -Z-cycloalkyl-, or -cycloalkyl-Z-, a 5- or 6-membered heterocyclic radical comprising 3–5 carbon atoms and 1 or 2 heteroatoms selected from N, O and S, or a $R^5$-substituted heterocyclic radical, wherein aryl is

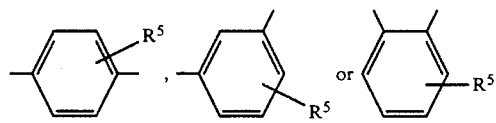

and cycloalkyl is

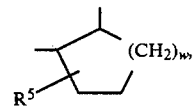

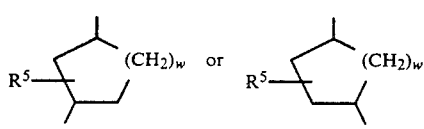

wherein w is 1, 2 or 3;

M is —$(CH_2)_u$— or —$((CH_2)_r$—X—$(CH_2)_v)$—;

W is

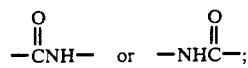

X and Z are independently a chemical bond, $-NR^9-$, $-O-$, $-S-$,

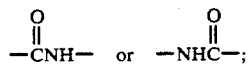

s, u and v are independently 0–5;
t is 1–5;
$R^1$, $R^2$ and $R^9$ are independently hydrogen, lower alkyl or lower acyl;
$R^3$ is hydrogen, lower alkyl, halo- and dihaloloweralkyl, trifluoroethylthiomethyl, phenylloweralkyl, (cycloalkyl)lower alkyl, aminomethyl, loweralkylaminomethyl, phenyl(lower)alkylthiomethyl, (cycloalkyl)loweralkylaminomethyl, 2-, 3- or 4-pyridylloweralkyl, 2-, 4- or 5-, thiazolyloweralkyl, 2-, 4- or 5-1H-imidazolylloweralyl, 1-imidazolylloweralkyl, 1-morpholinoloweralkyl or hydroxyphenylloweralkyl;
$R^4$ is chlorine or $CF_3$;
$R^5$ is hydrogen, halogen, lower alkyl, lower acyl, lower alkoxy, haloloweralkyl or phenylloweralkyl;
$R^7$ is hydrogen, lower alkyl or aminoloweralkyl;
$R^6$ and $R^8$ are independently hydroxy, alkoxy having from 1 to 8 carbon atoms, benzyl, allyl, $R^{10}-O-r-(CH_2)_m-O-$, wherein O is oxygen or sulfur, r is 0 or 1 and m is 2 to 4,

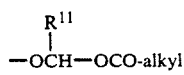

wherein the alkyl has from 3 to 8 carbon atoms,

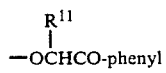

wherein the phenyl may be substituted with group T defined below, 1-glyceryl,

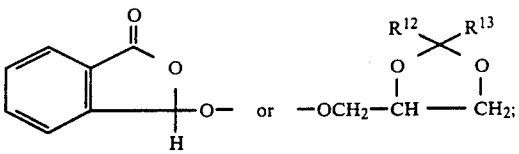

$R^{10}$ is phenyl, substituted phenyl wherein the substituents are chosen from group T, 1-naphthyl or 2-naphthyl;
T is halogen, hydroxy, trifluoromethyl, lower alkoxy, lower alkyl, 2-furanyl, 3-furanyl, 2-thienyl, 3-thienyl, phenyl and substituted phenyl wherein the substituents are chosen from halogen, hydroxy, trifluoromethyl, lower alkoxy or lower alkyl;
$R^{11}$ is hydrogen or alkyl having from 1 to 8 carbon atoms;
$R^{12}$ is hydrogen, lower alkyl, unsubstituted or substituted phenyl and substituted or unsubstituted phenyl lower alkyl, wherein phenyl may be substituted by group T; and
$R^{13}$ is hydrogen or lower alkyl;
provided that if L is alkenylene or alkynylene, J is $-(CH_2)_s-$ wherein s is 1–5; provided that if L is -Z-aryl-or -Z-cycloalkyl-, J is $-(CH_2)_s-$ wherein s is 2–5; provided that if L is alkenylene, alkynylene; -aryl-Z- or -cycloalkyl-Z-, M is $-(CH_2)_u-$ wherein u is 1–5; provided that if s and u are each zero, L is aryl or cycloalkyl (i.e. Z is a bond); and provided that if s and v are each zero, L is aryl or cycloalkyl (i.e. Z is a bond).

7. A composition according to claim 6 wherein said beta adrenergic blocking agent is selected from atenolol, metoprolol, nadolol, pindolol, propranolol, timolol, labetalol, betaxolol, carteolol, bunolol or dilevatlol, or pharmaceutically acceptable salts and/or isomers thereof.

8. A composition according to claim 6 wherein said beta adrenergic blocking agent is timolol.

9. A composition according to claim 6 wherein said beta adrenergic blocking agent is bunolol.

* * * * *